United States Patent [19]
Katti et al.

[11] Patent Number: 5,876,693
[45] Date of Patent: Mar. 2, 1999

[54] HYDROXYALKYL PHOSPHINE COMPOUNDS FOR USE AS DIAGNOSTIC AND THERAPEUTIC PHARMACEUTICALS

[75] Inventors: Kattesh V. Katti; Prahlad R. Singh; V. Sreenivasa Reddy; Kavita K. Katti; Wynn A. Volkert; Alan R. Ketring, all of Columbia, Mo.

[73] Assignee: The Curators of the University of Missouri, Columbia, Mo.

[21] Appl. No.: 902,829

[22] Filed: Jul. 30, 1997

Related U.S. Application Data

[63] Continuation of Ser. No. 412,470, Mar. 25, 1995, abandoned.

[51] Int. Cl.$^6$ ............................... A61K 51/04; C07F 5/00
[52] U.S. Cl. ............................ 424/1.65; 534/10; 534/11; 534/14; 424/1.77
[58] Field of Search ................................ 424/1.65, 1.77, 424/1.49, 1.69; 534/10, 11, 14

[56] References Cited

U.S. PATENT DOCUMENTS

| | | | |
|---|---|---|---|
| 4,419,339 | 12/1983 | Neirinckx | 424/1.11 |
| 4,439,196 | 3/1984 | Higuchi | 604/890 |
| 4,446,224 | 5/1984 | DeCant, Jr. et al. | 604/67 |
| 4,447,233 | 5/1984 | Mayfield | 604/152 |
| 4,475,196 | 10/1984 | La Zor | 371/29.1 |
| 4,486,194 | 12/1984 | Ferrara | 604/308 |
| 4,487,603 | 12/1984 | Harris | 604/152 |
| 4,795,626 | 1/1989 | Deutsch et al. | 424/1.11 |

OTHER PUBLICATIONS

Chatt et al. "Rhodium (I), Rhodium (II), Palladium (II) Complexes containing ligands of the type PRnQ3–n," J. Chem. Soc., (19), pp. 2021–2028 1973.
Chianelli et al. "99mTc–interlikin–2: a new radiopharmaceutical for the in vivo detection of lymphocytic infiltration" *J Nucl Biol Med* 38:476 (1994).
Deutsch, "Aspects of the chemistry of technetium phosphine complexes" *Radiochim Acta* 63:195–197, (1993).
Ellis et al., "Water–soluble tris(Hydroxymethyl) phosphine complexes with nickel, palladim and platinum . . . " *Inorg Chem* 31:3026–3033, (1992).
Fritzberg et al., "Specific and stable labeling of antibodies with 99mTc with a dimide dithiolate chelating agent" *Proc. Natl. Acad. Sci., USA* 85:4025–4029, (1988).
Gustavson et al., "Synthesis of a new class of Tc–chelating agents . . . " *Tetrahedron Lett*, vol. 32, No. 40, pp.5485–5488 (1991).
Jurisson et al., "Coordination compounds in nuclear medicine" *Chem Rev* 93:1137–1156, (1993).

Kelly et al., Technetium–99m–Tetrofosmin as a new radiopharmaceutical for myocardial perfusion imaging *J Nucl Med* 34:222–227 (1993).
Knight et al., "Thrombus imaging with 99mTc synthetic peptides based upon the binding domain of a monoclonal antibody . . . " *J Nucl Med* 35:282–288, (1994).
Lister–James et al., "A structure–activity–relationship (SAR) study of somatostatin receptor–binding peptides . . . " *J Nucl Med*, 35:257–258P, (1994).
Marmion et al., "Radiopharmaceutical development of TechneScan Q–12" *J Nucl Biol Med* 38:455–456, (1994).
Meares et al., "Chelate radiochemistry: cleavable linkers lead to altered levels of radioactivity in the liver" *Int J Cancer* 2:99–102, (1988).
Maina et al.,"Synthesis, radiochemical and biological evaluation of 99mTc[N4(O)Phe]–octreotide . . . " *J Nucl Bio Med* 38:452, (1994).
Nock et al., "99mTc–N4–Lys–Biotin, a new biotin derivative useful for pretargeted avidin–biotin immunoscintigraphy . . . " *J Nucl Biol Med* 38:460, (1994).
Nowotnik and Nunn, "Technetium SPECT agents for imaging heart and brain" *DN and P* 5:174–183, (1992).
Parker, "Tumour targeting with radiolabeled macrocycle–antibody conjugates" *Chem. Soc. Rev.* 19:271–291, (1990).
Pasqualini et al., "Bis(dithiocarbamato)nitrido technetium–99m radidpharmaceuticals: a class of neutral myocardial . . . " *J. Nucl. Med.* 35: 334–340 (1994).
Rao et al., "Kinetics and mechanism of reactions of S–protected dithiol monoaminemonoamide (MAMA) ligands with technetium" *Nucl Med Biol*, 19:889–895, (1992).
Troutner, "Chemical and physical properties of radionuclides" *Nucl Med Biol* 14:171 (1987).
Volkert et al., "Therapeutic radionuclides: production and decay property considerations" *J Nucl Med* 32:174–185, (1991).
Wilbur, "Radiohalogenation of proteins: an overview of radionuclides, labeling methods and reagents for conjugate labeling" *Bioconj Chem* 3:433–470, (1992).
Abrams et al., "Technetium–99m–human polyclonal IgG radiolabeled via the hydrzaino nicotinamide . . . " *J Nucl Med* 31:2022–2028, (1990).
Abrams et al. "Synthesis and crystal and molecular structure of a technetium–hydralazino complex . . . " *Inorg Chim Acta* 173:1333–135, (1990).

*Primary Examiner*—Gary E. Hollinden
*Assistant Examiner*—Michael G. Hartley
*Attorney, Agent, or Firm*—Kohn & Associates

[57] ABSTRACT

A compound and method of making a compound for use as a diagnostic or therapeutic pharmaceutical comprises a functionalized hydroxyalkyl phosphine ligand and a metal combined with the ligand.

4 Claims, 12 Drawing Sheets

SCHEME 1
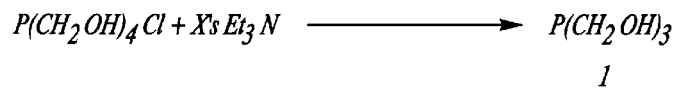
Fig-1
SCHEME 2
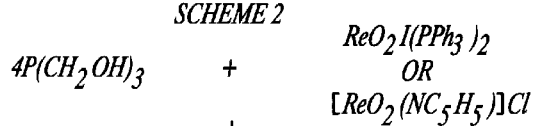
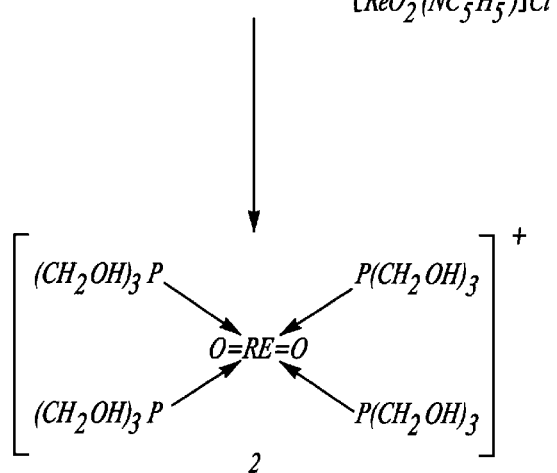
Fig-2
SCHEME 3
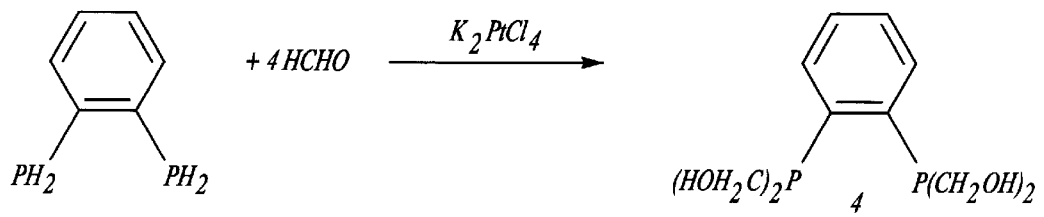
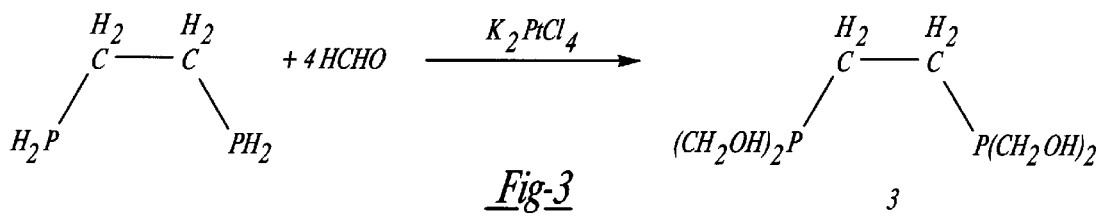
Fig-3

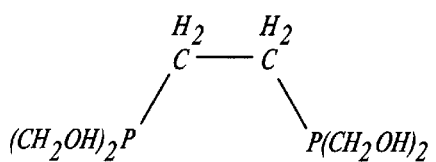
SCHEME 4
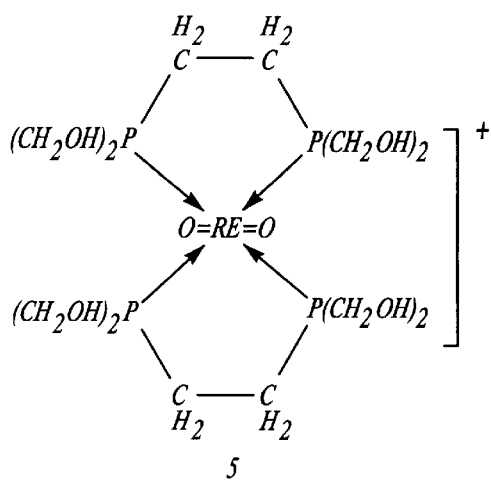
Fig-4
SCHEME 5
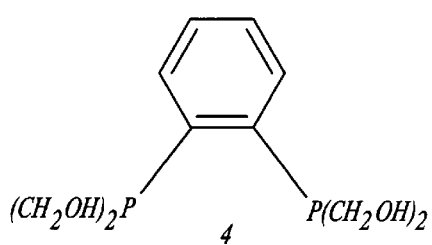
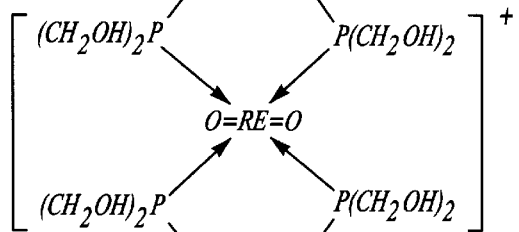
Fig-5

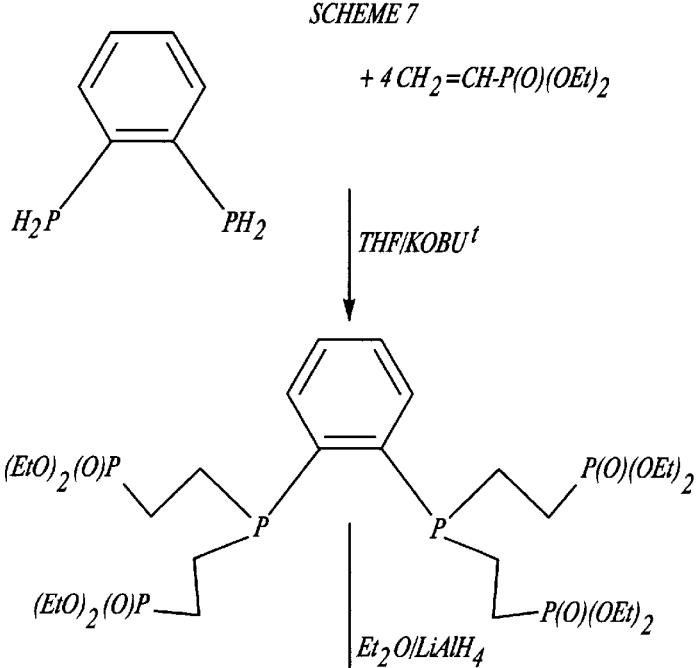
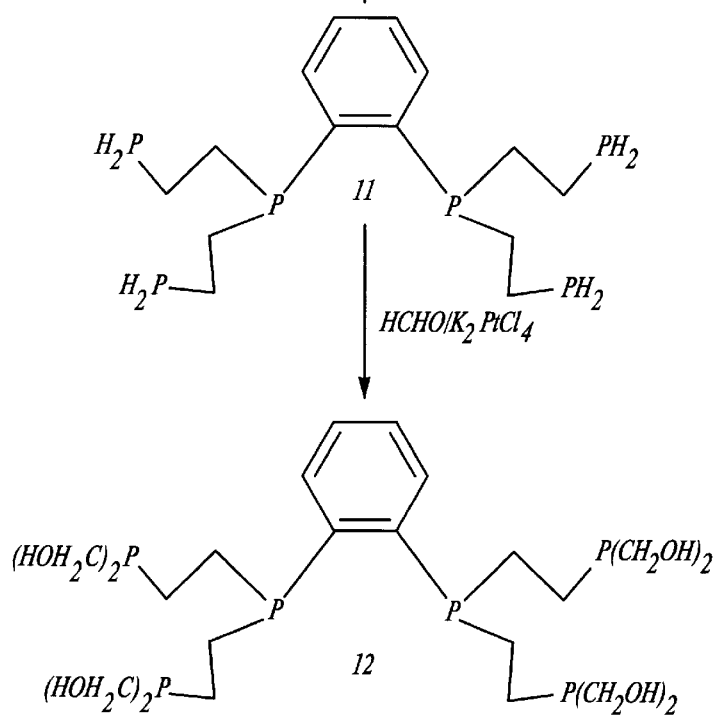
*Fig-6*
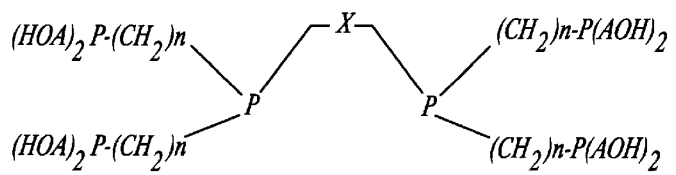
*Fig-7*

Fig-13  $^{31}P$ NMR SPECTRUM OF $(HOH_2C)_2PC_6H_4P(CH_2OH)_2$

Fig-14  $^{31}P$ NMR SPECTRUM OF $[Re(O)_2\{P(CH_2OH)_3\}]^+$ $^{31}P$ NMR SPECTRUM OF $[Re(O)_2\{HOH_2C)_2PC_6H_4P(CH_2OH)_2\}_2]^+$ 5,876,693

HYDROXYALKYL PHOSPHINE COMPOUNDS FOR USE AS DIAGNOSTIC AND THERAPEUTIC PHARMACEUTICALS

This application is a continuation of application Ser. No. 08/412,470, filed Mar. 25, 1995, now abandoned.

GRANT REFERENCE

The research carried out in connection with this invention was supported in part by a grant from the Department of Energy (DOE-DEFG0289ER60875). The Government has certain rights in the invention.

BACKGROUND OF THE INVENTION

1. Technical Field

The present invention relates to pharmaceuticals, and especially radiopharmaceuticals for use as diagnostic and therapeutic agents. More specifically, the present invention relates to compounds and methods of synthesizing compounds which utilize both mono- and multi-dentate ligands which form stable complexes with metal compounds without the need for external reducing agents for use as diagnostic or therapeutic radiopharmaceuticals.

2. Background Art

Because of the favorable physical properties, widespread availability, and low cost of $^{99m}$Tc, this radionuclide continues to be the most attractive candidate to formulate diagnostic radiopharmaceuticals for scintigraphic imaging studies in patients (Jurisson et al., 1993). Re, a chemical analogue of Tc, has two radioisotopes (i. e., $^{186}$Re and $^{188}$Re; $^{186/188}$Re) that have physical and production properties that make them among the most attractive beta-emitting radionuclides for formulation of new therapeutic radiopharmaceuticals (Volkert et al., 1991; Troutner, 1987). $^{105}$Rh is another important beta-emitting radionuclide for use in preparing therapeutic radiopharmaceuticals (Troutner, 1987). Since the chemical properties of Tc and Re are often identical (although, not always) many ligand systems can be used as a basis to synthesize bifunctional chelating agents (BFCAs) that are capable of forming chelates with $^{99m}$Tc that have the same structural and physicochemical properties as the corresponding $^{186/188}$Re chelates.

Development of sophisticated molecular probes in the design of new $^{99m}$Tc-, $^{186/188}$Re, and $^{105}$Rh radiopharmaceuticals will provide for future advances in the diagnosis and treatment of patients. While many important single photon emission computed tomography (SPECT) radiopharmaceuticals are effectively used as specific tools for diagnosis of human disease, accelerated development of many new site-directed synthetic derivatives (e.g., immunologically derived molecules, receptor-avid molecules, etc.) will provide a multitude of opportunities for further technological advances for both diagnostic and therapeutic applications. Many difficulties encountered in the design of highly selective radiolabeled drug carriers must be overcome (e.g., problems in efficient drug delivery to target sites, in vivo metabolism, rates of clearance of radioactivity from non-target tissues relative to target tissues, etc.). The physicochemical characteristics of the $^{99m}$Tc-, $^{105}$Rh-, and $^{186/188}$Re-chelate moiety attached or fused to the site-directed molecule will play a crucial role as an inherent determinant of the effectiveness of the final drug product. In addition, the ability of $^{99m}$Tc or $^{186/188}$Re to label the final product under conditions amenable for routine formulation of radiopharmaceuticals is also an essential consideration.

Labeling of biomolecules with $^{99m}$Tc or $^{186/188}$Re to produce effective radiopharmaceuticals presents many challenges. It is necessary to produce $^{99m}$Tc and/or $^{186/188}$Re labeled drugs that have high in vitro and in vivo stabilities. Several different ligand frameworks have been developed that form $^{99m}$Tc or Re chelates exhibiting minimal or no measurable in vivo or in vitro dissociation. These chelates have provided radiopharmaceutical chemists with a selection of $^{99m}$Tc-chelates that have a range of physicochemical characteristics. The formation of $^{99m}$Tc (viz Re) products in high yields with high radiochemical purity (RCP), however, usually requires the presence of large quantities of excess ligand during the formulation processes that are used for routine pharmaceutical preparation. Unfortunately, the high specific activities (i.e., GBq/µmole or Ci/µmole) required for radiolabeled site-directed synthetic derivatives being developed precludes the use of many of these chelation systems, thus, severely limiting the choice to only a few ligand backbones.

High specific activity (Sp. Act) radiolabeled agents can be prepared using either preformed $^{99m}$Tc- or $^{186/188}$Re bifunctional chelates (BFCs) or post-conjugation chelation with the radioactive metals where a chelating moiety is already appended (Parker, 1990) or fused (Lister-James et al., 1994; Knight et al., 1994) to the biomolecular targeting agent. Even though maximization of Sp. Act can be achieved by separation of the radiolabeled from the non-radiolabeled molecules, practically it is more desirable to employ chelation systems that require small quantities of the chelates. In the formation of products that will be ultimately used as FDA approved $^{99m}$Tc/$^{186/188}$Re radiopharmaceuticals for routine patient care applications, it is most desirable to keep the number of steps for the formation of the drug-product to a minimum, ideally to one step, as is the case for most $^{99m}$Tc- "instant kits".

One of the few ligand systems shown to be effective for preparation of high yield, stable $^{99m}$Tc chelates using small quantities of chelator are the amido-thiol class of ligands (Fritzberg et al. 1988, Rao et al., 1992, and Chianelli et al, 1994). Generally, these types of multi-dentate ligands contain at least four donor atoms and one or two thiol donor groups in combination with 2–3 amido donor groups. Several $N_2S_2$ or $N_3S$ amido-thiol frameworks have been used to synthesize BFCAs and include diamido-dithiol (DADS) ligands (Fritzberg et al., 1988), monoaminemonoamide (MAMA) ligands (Rao et al., 1992; Gustavson et al., 1991) and mecaptoacetylglycylglycyl-glycine ($MAG_3$) ligands (Chianelli et al., 1994). While the amido-thiol ligands make effective BFCAs for $^{99m}$Tc and $^{186/188}$Re, the range of their physicochemical properties are limited, conditions for routine labeling can be difficult to reduce to practical utility and external reducing agents (e.g., Sn(II)) are usually present during labeling with $^{99m}$Tc or $^{186/188}$Re, which can cause irreversible alteration of the site-directed moiety reducing or eliminating specific in vivo localization.

Other ligand systems that have also been used for $^{99m}$Tc labeling include $N_2S_2$-amine-thiol ligands, propylineaminoeoxime (PnAO) derivatives and the hydrazino nicotinamide (HYNIC) system. The former two derivatives form neutral lipophilic $^{99m}$Tc-chelates, that while beneficial in some respects, result in high non-specific binding in vivo and poor clearance from non-target tissues (Muna et al., 1994; Noch et al., 1994). The HYNIC system does not form a well-defined product with $^{99m}$Tc (Abrams et al., 1990a; Abrams et al., 1990b). All of these systems usually form chelates with $^{99m}$Tc with the necessity of external reducing agents.

Ligand backbones containing trivalent phosphine donor groups have been shown to be effective in forming stable $^{99m}$Tc and $^{186/188}$Re chelates in high RCP. Phosphines not only chelate $^{99m}$Tc (or Re), but they are capable of reducing both pertechnetate and perrhenate to lower oxidation states, and, therefore, do not necessarily require the presence of an external reducing agent [e.g., Sn(II)]. Diphosphine ligands have been extensively used in the development of $^{99m}$Tc-radiopharmaceuticals, particularly those that are used as $^{99m}$Tc-labeled myocardial perfusion agents (Deutsch, 1993; Nowotnik and Nunn, 1992; Kelly et al., 1993). Unfortunately, most of these chelates utilize alkyl-phosphine donor groups and the phosphines are rapidly oxidized (to phosphorus oxides) in aqueous solutions containing $O_2$ and require stringent conditions for manufacture of the drugs and for ultimate routine formation of the final product. For these reasons, ligands that contain alkyl phosphine donor groups have limited flexibility for the design of new drugs and do not form a rational basis to prepare most phosphine-based BFCAs for use in preparing site-directed radiopharmaceuticals. Aromatic phosphines have also been reported for use with Tc and Re, however, the high lipophilicity of the resulting chelates minimize their potential utilization as BFCAs for in vivo applications.

A small ligand system containing phosphine donor groups with good solubility in aqueous solutions and not oxidized by $O_2$, but still capable of reducing $^{99m}$TcO$_4^-$ or $^{186/188}$ReO$_4^-$ and/or strongly chelating reduced Tc or Re, would find widespread applicability in formulating new radiopharmaceuticals or new BFCAs.

Most other bifunctional chelation systems require the presence of an external reducing agent (e.g., $Sn^{+2}$) or prereduction of $^{99m}$TcO$_4^-$ or $^{186/188}$ReO$_4^-$ to lower metal oxidation states (e.g. $^{99m}$Tc-glucoheptonate). Water soluble phosphine groups containing low molecular side arms attached to each phosphine P-atom would provide versatility in ligand design and could be used as both as a reducing agent for $^{99m}$TcO$_4^-$ (or $^{186/188}$ReO$_4^-$) under conditions used for routine $^{99m}$Tc-radiopharmaceutical preparation and as an efficient complexing agent for the reduced forms of Tc or Re.

Applicants use a mono-dentate phosphine ligand and a series of multi-dentate ligands containing functionalized hydroxyalkyl phosphines that are stable in aerated aqueous solutions and will form highly stable $^{99m}$Tc and $^{188}$Re chelates. Unlike prior art alkyl phosphine based ligands designed to reduce or chelate $^{99m}$Tc or $^{186/188}$Re, the hydroxyalkyl phosphine groups are not sensitive to the presence of oxygen when dissolved in aqueous solutions. Other water soluble phosphine ligands with good oxidative stability have also been used as reducing agents, however, the side chains attached to the phosphine donor P-atoms in these ligands are bulky and produce highly charged phosphines which limit their utility in radiopharmaceutical development (Pasqualine et al., 1994).

Most other bifunctional chelation systems require the presence of an external reducing agent (such as Sn(II) or NaBH$_4$) or prereduction in order to reduce the $^{99m}$TcO$_4^-$ (or $^{186/188}$ReO$_4^-$) from the +7 oxidation state to lower oxidation states (e.g., $^{99m}$Tc-GH) that are more readily chelated.

The ligands containing one or more hydroxyalkyl phosphine donor groups of the present invention require no external reducing agents, however, the ligand can be used as coordinating groups when used in conjunction with other reducing agents or $^{99m}$Tc-synthons. The resulting $^{99m}$Tc and Re complexes produced with these phosphine containing ligands exhibit excellent in vivo stability as well in aqueous solutions including human serum.

SUMMARY OF THE INVENTION AND ADVANTAGES

According to the present invention, there is provided a compound for use as diagnostic or therapeutic pharmaceuticals, the compound comprising a ligand and a metal combined with the ligand, the ligand comprising at least one hydroxyalkyl phosphine donor group and is capable of reducing the metal and thereby promoting formation of the compound.

The present invention further provides a method of making mono-dentate compounds for use as diagnostic and/or therapeutic pharmaceuticals, the method including the following reactions:

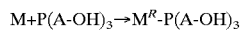

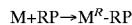

where M is a transition metal; $M^R$ is a transition metal in a reduced oxidation state as compared to M; RP is a non-labeled radiopharmaceutical precursor containing a complexing moiety for coordinating the reduced forms of the metals; and A is an alkyl group.

The present invention further provides a method of making multi-dentate compounds for use as diagnostic and/or therapeutic pharmaceuticals, the method including the following reactions:

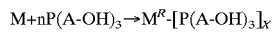

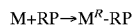

where M is a transition metal; $M^R$ is a transition metal in a reduced oxidation state as compared to M; X is 1–6; n=1–6; RP is a non-labeled radiopharmaceutical precursor containing a coordinating moiety for coordinating the reduced forms of the metals; and A is an alkyl group.

The present invention also provides mono-dentate and multi-dentate ligands containing at least one hydroxyalkyl phosphine donor group along with other donor atoms (e.g., N-, O-, S- and P-atoms) in the ligand framework to form $^{99m}$Tc or $^{186/188}$Re chelates in aerated aqueous solutions possessing in vitro and in vivo stability.

The present invention further provides methods of treatment utilizing mono-dentate and multi-dentate ligands containing at least one hydroxyalkyl phosphine group combined with a metal for diagnostic as well as therapeutic purposes.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 illustrates a synthesis scheme for synthesis of ligands containing one or more hydroxyalkyl phosphine groups in accordance with present invention;

FIG. 2 illustrates a synthesis scheme for the synthesis of Rhenium complexes in accordance with the present invention;

FIG. 3 illustrates a synthesis scheme for synthesis of bis-hydroxymethylphosphine containing ligands;

FIG. 4 illustrates a synthesis scheme for synthesis of metal complexes utilizing the ligands of FIG. 3;

FIG. 5 illustrates a synthesis scheme for synthesis of metal complexes utilizing the ligands of FIG. 3;

FIG. 6 illustrates a synthesis scheme for synthesis of a ligand containing six phosphine donor groups;

FIG. 7 illustrates a general structure for a ligand produced in FIG. 6;

DETAILED DESCRIPTION OF THE PREFERRED EMBODIMENT

Figure 8:
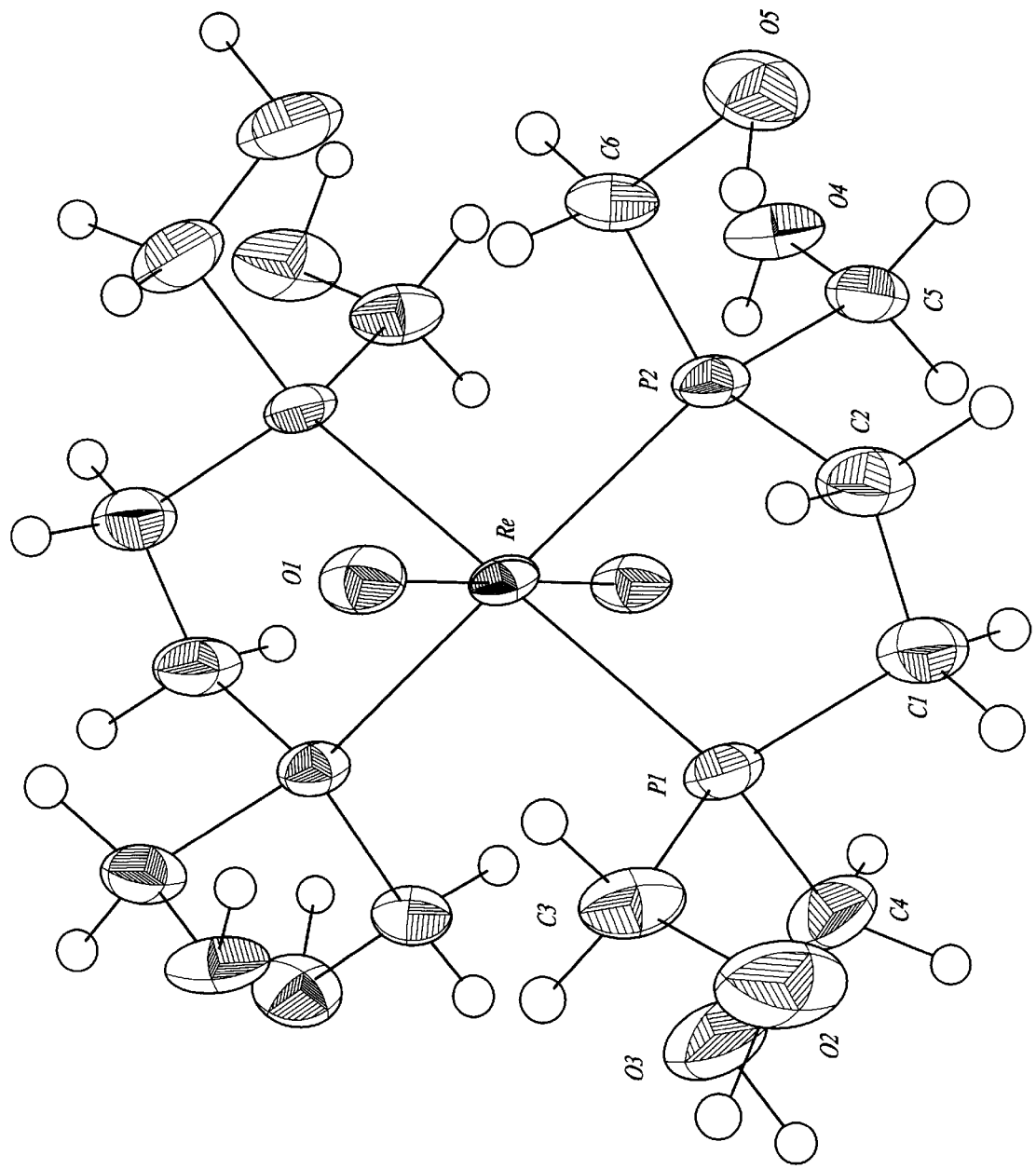
FIG. 8 illustrates the crystal structure of compound (5)

Generally, the present invention provides a compound for use as a diagnostic or therapeutic pharmaceutical however, the compounds can also be used for other pharmaceutical applications including MRI contrast agents. The novel compounds of the present invention provide labeled molecules which can be used as diagnostic and therapeutic radiopharmaceuticals. The compounds include a transition metal complexed with at least one ligand including coordination of the metal to one or more hydroxy alkyl phosphine donor groups. That is, the invention provides a phosphine-based ligand system typically containing between 1 and 6 hydroxyalkyl phosphine donor units for use in forming complexes with a variety of transition metals that have high in vitro and/or in vivo stability. The invention provides a hydroxyalkyl phosphine-based ligand system for use in forming complexes with a variety of transition metals that have high in vivo and/or in vitro stability in aerated aqueous solutions.

The compounds and method of producing the compounds of the present invention can be generally characterized by the formulas:

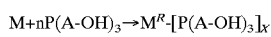

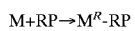

where M is a transition metal; M$^R$ is a transition metal in a reduced oxidation state as compared to M; X is 1–6; n=1–6; RP is a non-labeled radiopharmaceutical precursor containing a coordinating moiety for coordinating the reduced forms of the metals; and A is an alkyl group.

The ligand is complexed with the transition metal, generally from the group including $^{186/188}$Re, $^{105}$Rh, and $^{99m}$Tc. These complexes contain greater than or equal to ($\geq$) 1:1 ligand-to-metal ratios which is formed making the resulting chelates small and well-defined. These specific combinations permit the formation of the complexes in a one step, high yield reaction as described below, especially for use with readily available chemical forms of the radionuclides.

For example, $^{99m}$TcO$_4^-$, ReO$_4^-$ chelates or $^{105}$Rh-chloride can be used. It has been determined that these types of hydroxyalkyl phosphine ligands form highly stable chelates with a variety of transition metals that have radioactive isotopes which include γ and β emitting isotopes such as $^{186}$Re, $^{188}$Re, $^{109}$Pd, $^{105}$Rh, etc., or for diagnostic use such as with $^{99m}$Tc radiopharmaceuticals.

More specifically, the present invention provides methods to formulate mono- and multi-dentate $^{99m}$Tc- or $^{186/188}$Re-labeled molecules (chelates) for use as diagnostic or therapeutic radiopharmaceuticals, respectively. The ligands used in this technology include one or more hydroxy alkyl phosphine donor groups that can be used in reducing $^{99m}$Tc- or $^{186/188}$Re and/or coordinating $^{99m}$Tc, $^{186/188}$Re, or $^{105}$Rh. The hydroxyalkyl phosphine group(s) on the ligand are soluble in aqueous solutions and exhibit minimal or no significant oxidation by O$_2$. That is, the invention provides small air stable and water soluble phosphine based ligands for use in forming complexes with $^{99m}$Tc- or $^{186/188}$Re in high yields that have high in vitro and in vivo stability which are not sensitive to oxidation in the presence of O$_2$. $^{99m}$Tc or $^{186/188}$Re reactants can be in the form of oxides (including $^{99m}$TcO$_4^-$ or $^{186/188}$ReO$_4^-$) as well as in other forms of the metals.

The chelates made in accordance with the present invention have been found to be stable in aqueous solutions, serum and other body fluids. This is critical to solve the problems of prior art agents which did not form stable chelates thereby having an inherent loss of control of localization of the radionuclide paramagnetic metal. Further, compounds made in accordance with the present invention can be chemically modified, as discussed below, to provide for specificity of localization, increased physical half-life of the radionuclide, improved pharmacokinetics, and increased selectivity of target tissues, such as tumors, over normal tissue, such as bone marrow, kidney, G.I. tract, liver etc.

The compounds made in accordance with the present invention are not only stable in neutral aqueous solutions, but have also been found to be stable in acidic and basic aqueous media. Again, this is critical with regard to localization of the compound in areas of the body having different pH's, as well as being stable through different administration routes, such as oral administration.

The ligands produced in accordance with the present invention can be mono-dentate (one donor atom on the ligand) or can be multi-dentate (more than one donor atom per ligand molecule).

The general types of hydroxyalkyl phosphine containing ligands include mono-dentate hydroxyalkyl phosphine ligands, bidentate-bishydroxyalkyl phosphine ligands, and multi-dentate (i.e., no of chelating atoms or group $\geq$3) containing $\geq$1 hydroxyalkyl phosphine groups per metal. These ligands are used to form the stable, water soluble $^{99m}$Tc, $^{186/188}$Re, and $^{105}$Rh chelates of the present invention.

Mono-dentate ligands produced in accordance with the present invention are of the general formula:

wherein A is —CH$_2$—, —C$_2$H$_4$—, or iso- or normal —C$_3$H$_6$—.

In addition to the use of mono-dentate hydroxyalkyl phosphine ligands by themselves to form $^{99m}$Tc chelates for radiopharmaceutical preparations, mono-dentate hydroxyalkyl phosphine ligands can also be used in conjunction with other ligands used to chelate $^{99m}$Tc, $^{186/188}$Re, and $^{105}$Rh.

For example, the mono-dentate phosphine ligand tris (3-methoxy-1-propyl) phosphine was used in conjunction with 1,2-bis (dihydro-2,2,5,5-tetramethyl-3-furanone-4-methyleneamino) ethane to complex $^{99m}$Tc to form a ($^{99m}$Tc- Q12) lipophilic-cationic (+1) complex. This complex is being evaluated for use as a myocardial perfusion radiopharmaceutical (Marmion et al., 1994). In this complex, the mono-dentate phosphine ligand is bound in the trans positions to the metal (Deutsch, 1993; Marmion et al., 1994). The ether side chains on this phosphine ligand increase the lipophilicity of the $^{99m}$Tc chelate in order to improve myocardial uptake. The mono-dentate hydroxyalkyl phosphine ligands described in the present invention can be used in a similar manner, however, in contrast to the prior art mono-dentate phosphine ligands, the hydroxyalkyl phosphine ligand increases aqueous solubility of the complex for improved clearance into the urine via the kidneys.

Bi-dentate hydroxyalkyl phosphine ligands used produced in accordance with the present invention are characterized by the following formula:

(HOA)$_2$P—X—P (AOH)$_2$ where A=—CH$_2$—, —(CH$_2$)$_2$—, or iso- or normal- C$_3$H$_6$— and X includes —(CH$_2$)$_n$— where n=1–4, —CH$_2$CHR—, —CH$_2$CHRCH$_2$—, —CHRCH$_2$CH$_2$—, substituted aromatic where R is an appended side-arm for modification of the physico-chemical characteristics (e.g., polarity, charge, etc.) of the final $^{99m}$Tc- or $^{186/188}$Re- chelate or for linking the chelate to a bio-selective targeting moiety (e.g., MAb, receptor agent), R can be H, an alkyl group (C$_1$–C$_4$), an aromatic group, and/or contain a functional group such as —OH, —NH$_2$, —COOH, —SH, and other groups used for conjugation of uncomplexed ligand or "preformed" $^{99m}$Tc or $^{186/188}$Re complex of the BFCA to the biomolecular targeting structure.

Methods used for conjugation of chelates to biomolecules involve activation (e.g., to activated esters, N-hydroxysuccinimides, benzyl isothiocyanate, alkyl halides, CDI (cyclohexyl diimide), etc.) of the functional groups that have been previously described (Meares et al., 1988; Parker, 1990; Wilbur, 1992).

Formation of $^{99m}$Tc (and $^{186/188}$Re) can be performed by reduction of $^{99m}$TcO$_4^-$ or $^{188}$ReO$_4^-$ by excess of the phosphine ligand, an external reducing agent [e.g., Sn(II)] or by transchelation.

In an alternative embodiment of the present invention, multi-dentate hydroxyalkyl phosphine based ligands can be used to form $^{99m}$Tc or $^{186/188}$Re complexes in aqueous systems by transchelation from weaker donor chelates (e.g., $^{99m}$Tc(V)-glucoheptonate, $^{186/188}$Re(V)-citrate, $^{99m}$Tc-P(CH$_2$OH)$_3$), following reduction with external reducing agents (e.g., Sn$^{+2}$), or without external reducing agents. This approach utilizes ligand frameworks containing greater than or equal to ($\geq$) one (1) hydroxyalkyl phosphine donor group(s). In one such embodiment, a hydroxyalkyl phosphine donor group on a multi-dentate ligand backbone is utilized so that the phosphine functionality of the molecule reduces $^{99m}$TcO$_4^-$ or $^{186/188}$ReO$_4^-$ and the other intramolecular phosphines or other donor atoms (e.g., —N, —O, —P or —S atoms) interact to form stable chelates with the reduced radiometals.

Most of the hydroxyalkyl phosphine containing ligands used to form BFCAs are multi-dentate (i.e., $\geq$3 donor atoms) and, generally, form 1:1 ligand-to-metal complexes with the reduced (i.e., oxidation states <+7) $^{99m}$Tc, $^{186/188}$Re, and $^{105}$Rh.

Hydroxyalkyl phosphine ligands with lower denticity can form $^{99m}$Tc or $^{186/188}$Re chelates with metal-to-ligand ratios greater than (>) 1:1 which also can be utilized in the formation of radiopharmaceuticals.

Generally, multi-dentate phosphine-based ligands are a preferred embodiment of the present invention since they are capable of forming 1:1 metal-to-ligand ratio complexes with $^{99m}$Tc or $^{186/188}$Re. The ability to form 1:1 ratio metal-to-ligand complexes permits formation of $^{99m}$Tc or $^{186/188}$Re chelates that form an essential component of well-defined diagnostic or therapeutic radiopharmaceuticals.

The hydroxyalkyl-phosphine based ligands are advantageous since they permit labeling of compounds with $^{99m}$Tc or $^{186/188}$Re in aerated aqueous media in the neutral pH range. In addition, the hydroxyalkyl phosphine based ligands promote the formation of highly stable chelates by simply mixing $^{99m}$TcO$_4^-$ or $^{186/188}$ReO$_4^{4-}$ with the ligand. This is advantageous since radio-pharmaceuticals generally are prepared just prior to their administration in order to provide maximum isotope activity. This can occur over a wide pH range, in the presence of O$_2$, and in the absence of external reducing agents (e.g., Sn$^{+2}$). These properties make hydroxy alkyl phosphine based ligands particularly useful and versatile for the formulation of new and unique $^{99m}$Tc or $^{186/188}$Re commercial drug products for routine use in human patients.

Multi-dentate Ligands Containing HydroxyalkylPhosphine Groups

Multi-dentate ligands used in accordance with the present invention can be characterized by wide variety of formulae. One class of ligands includes ligand frameworks in which only phosphine groups are used as donor sets to coordinate $^{99m}$Tc or $^{186/188}$Re. The other class utilizes ligand backbones containing the hydroxyalkyl phosphine group(s) along with other donor atoms (e.g., S, N, P, or O) or groups (e.g., amines, amides, thiols, carboxyls or hydroxyls) are used to coordinate the metals.

Ligands Containing Multiple Phosphine Groups

Several examples of ligands containing greater than or equal to ($\geq$) three (3) phosphine groups capable of binding $^{99m}$Tc or $^{186/188}$Re can be envisioned. For example, ligands containing six phosphone functionalities can be characterized by the following formula:

[(HOA)$_2$PY]$_2$—P—X—P[YP(AOH)$_2$]$_2$ where A=—CH$_2$—, —(CH$_2$)$_2$—, iso- or normal-C$_3$H$_6$— and X includes groups consisting of —CH$_2$—, —(CH$_2$)$_2$—, —(CH$_2$)$_3$—, —(CH$_2$)$_4$—, —CH$_2$CHR—, —CH$_2$CHRCH$_2$—, —CHRCH$_2$CH$_2$—, substituted aromatic group where R is an appended side-arm for modification of the physicochemical characteristics of the final $^{99m}$Tc or $^{186/188}$Re chelates or for linking the chelate to a bioselective targeting moiety. R and be H, an alkyl group (C$_1$–C$_4$), an aromatic group and/or contain a functional group, such as —OH, —NH$_2$, —COOH, —SH, and other groups that can be used for conjugation of the uncomplexed or the "preformed" $^{99m}$Tc or $^{186/188}$Re chelate to biomolecular targeting structures. Methods and groups that can be used for conjugation involve activation of functional groups (e.g., to activated esters, N-hydroxy-succinimides, benzylisothiocyanate alkyl halides, CDI (cyclohexyl diimide), etc.) using approaches that have been previously described (Meares et al., 1988; Parker, 1990; Wilbur, 1992). Y is —CH$_2$, —C$_2$H$_4$—, or —C$_3$H$_6$.

Formation of $^{99m}$Tc (and $^{186/188}$Re) chelates with these ligands can be effected by reduction of $^{99m}$TcO$_4^-$ or $^{186/188}$ReO$_4^-$ with one of the phosphine groups with subsequent chelation by the other intramolecular phosphine groups. This type of chelate formation is novel in that it provides a unique situation where the same ligand that reduces $^{99m}$TcO$_4^-$ or $^{186/188}$ReO$_4^-$ can in turn immediately complex the reduced metals thereby eliminating the need for external reducing agents and their associated problems. Other more standard methods, well known in the art, for $^{99m}$Tc and $^{186/188}$Re complexation with these ligands can also be used including complex formation by transchelation or using external reducing agents (i.e., Sn(II) dithionite, HCl, etc.).

Another example of a multi-dentate ligand according to the present is a hexadentate compound of the formula:

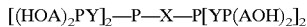

wherein A is —CH$_2$—, —C$_2$H$_4$—, or iso- or normal-C$_3$H$_6$—; and X is —(CH$_2$)$_n$— where (n=1–4), —CH$_2$CHR—, —CH$_2$CHRCH$_2$—, —CHRCH$_2$CH$_2$—, or R-aromatic where R is H, an alkyl group of C$_1$–C$_4$, an aromatic group, —OH, —SH, —NH$_2$, —COOH, activated esters, N-hydroxysuccinimides, benzyl isothiocyanate, alkyl halides, or CDI; and Y is CH$_2$—, —C$_2$H$_4$—, or —C$_3$H$_6$—.

In this particular multi-dentate compound, the ligands can all include phosphine donor groups. Alternatively, the ligands can include at least one donor group which is substituted for greater than or equal to ($\geq$) one (1) phosphine groups. The chelating groups can include two donor atoms which are hydroxyalkyl phosphine P-atoms and two donor atoms which are atoms other than P-atoms and have the formula:

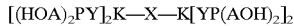

wherein A is —CH$_2$—, —(CH$_2$)$_2$—, or iso- or normal-C$_3$H$_6$—; K is donor atoms including —N(R)—, N(H)—, —Ag—, and S; X is —CH$_2$—, —(CH$_2$)$_2$—, —(CH$_2$)$_3$—, —(CH$_2$)$_4$—, —CH$_2$CHR—, —CH$_2$CHRCH$_2$—, —CHRCH$_2$CH$_2$—, or R'-aromatic where R' and R can be the same or different and are selected from H, —OH, —SH, —NH$_2$, —COOH, activated esters, N-hydroxysuccinimides, benzyl isothiocyanate, alkyl halides, or cyclohexyl diimide; and Y is —CH$_2$—, —(CH$_2$)$_2$—, or iso- or normal-C$_3$H$_6$—.

Alternatively, the coordinating groups can include two donor atoms which are hydroxyalkyl phosphine P-atoms and two donor atoms which are atoms are N-atoms and have the general formula:

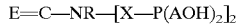

wherein X is —CH$_2$—, —(CH$_2$)$_2$—, —C$_3$H$_6$—; A is —CH$_2$—, —(CH$_2$)$_2$—, —C$_3$H$_6$—; E is O or S; R can be the same or different and is selected from H, —OH, —SH, —NH$_2$, —COOH, activated esters, N-hydroxysuccinimides, benzyl isothiocyanate, alkyl halides, or cyclohexyl diimide; and Y is —CH$_2$—, —(CH$_2$)$_2$—, or iso- or normal-C$_3$H$_6$—.

Compounds containing hydroxyalkyl phosphine donor groups made in accordance with the present invention can also be chemically modified or linked with site specific biomolecules to produce specificity of tissue localization, improved pharmacokinetics, and increased selectivity of target tissues such as tumors over normal tissues which include, but are not limited to, bone marrow, kidney, G.I. tract, and liver.

The above formulas characterize the present invention as being very modifiable in order to specifically tailor the ligand for chelation with a specific radionuclide and localization at a specific target organ.

For example, the ligand can be conjugated to proteins or antibodies and can use side chains previously used for linking monoclonal antibodies. For example, conjugation reactions can involve reactive groups such as benzyl isothiocyanate, bromoacetamide, activated esters, N-hydroxysuccinimides, cleavable ester linkages, and aldehydes. Accordingly, a single monoclonal antibody or several monoclonal antibodies can be added to the metal-ligand complex to provide specificity of the binding of the ligand metal complex to specific surface antigen or target tissue.

As discussed above, other side chain modifications can be accomplished to make the chelate more polar and hydrophilic. For example, charged groups such as carboxyl or hydroxyl groups can be added at the various R groups appended to the phosphine groups. This additional small change in the compounds providing charged/polar groups increases the hydrophilic character of the resulting chelate. This will produce more rapid and selective clearance from the blood and nontarget tissue. This modification is highly desirable for the promotion of efficient clearance of radioactivity from nontarget tissues, such as blood, liver, kidney, and spleen following catabolism of conjugated radiolabeled monoclonal antibodies that are presently used for therapy.

Alternatively, the hydrophobicity of the chelate can be varied incrementally by varying the alkyl chain length of the side chains appended to the phosphine groups. For example, the alkyl groups on the phosphine moiety can be derivatized with for example methyl, ethyl, and n- or i-propyl. This is desirable because with some chelates, particularly those labeled with $^{99m}$Tc, an increase in the hydrophobicity of the chelate plays a major role in targeting uptake in selective tissues, such as in brain, heart and lung. Addition of alkyl groups to the chelating backbone increases the lipid solubility of the chelate. If the resulting chelate is neutral, either brain, heart, or lung imaging agents can be developed.

An alternative to varying the alkyl chain length of the R groups appended to the phosphine moieties is to add other functional groups, such as —OH, —SH, —NH$_2$, —COOH, activated esters, N-hydroxysuccinimides benzyl isothiocyanate, alkyl halides, or cyclohexyl diimide. The use of ether substitutions instead of the alkyl side chains will increase lipophilicity but also improves the rate of clearance of the chelate from the blood and other non-target tissues.

All of the aforementioned modifications demonstrate the flexibility of compounds made in accordance with the present invention and further the ability to modify these compounds to alter the binding, elimination, and absorption of the compounds in order to tailor the compounds for specific organ targeting, dosing, and metabolism.

The compounds produced in accordance with the present invention can be utilized by methods well known in the art as radio-pharmaceuticals for either radio-imaging or therapeutic treatment of diseases such as cancers, infections, neurological disorders, cardiac diseases, and further includes a wide variety of disorders that are currently evaluated in nuclear medicine laboratories. $^{99}$Tc can be used for all diagnostic imaging studies while $^{105}$Rh and $^{186/188}$Re can only be used therapeutically for treatment primarily of cancers.

The compounds produced in accordance with the present invention are administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art.

In the method of the present invention, the metal-hydroxyalkyl containing compounds (complexes) can be administered in various ways. It should be noted that the compounds can be administered as the compound or as pharmaceutically acceptable salt and can be administered alone or in combination with pharmaceutically acceptable carriers. The compounds can be administered orally or parenterally including intravenous, intraperitoneally, intranasal and subcutaneous administration. Implants of the compounds are also useful. The patient being treated is a warm-blooded animal and, in particular, mammals including man.

When administering the metal-hydroxyalkyl containing compounds parenterally, the pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like.

According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the metal-hydroxyalkyl containing compounds can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

A pharmacological formulation of the metal-ligand compounds utilized in the present invention can be administered orally to the patient. Conventional methods such as administering the compounds in suspensions, solutions, emulsions, syrups and the like are usable. Known techniques which deliver the metal-ligand compounds orally or intravenously and retain the biological activity are preferred.

The following are examples of ligands and chelates formed in accordance with the present invention.

EXAMPLES

Ligands Synthesized

Example 1
Mono-dentate Alkylphosphine Ligands

The mono-dentate hydroxyalkylphosphine ligands produced in accordance with the present invention can be characterized by the following formula:

$$P(AOH)_3$$

Mono-dentate hydroxyalkyl phosphines where A=—$CH_2$—, —$(CH_2)_2$—, iso- and normal- $C_3H_6$—.

A trihydroxymethylphosphine ligand of formula (1), as shown in FIG. 1, was prepared by the method described below while other short chained trihydroxymethylphosphine ligands can be prepared by methods previously described (Ellis et al., 1992).

Synthesis of Tris(hydroxymethyl)phosphine, $P(CH_2OH)_3$ (1)

Figure 11:
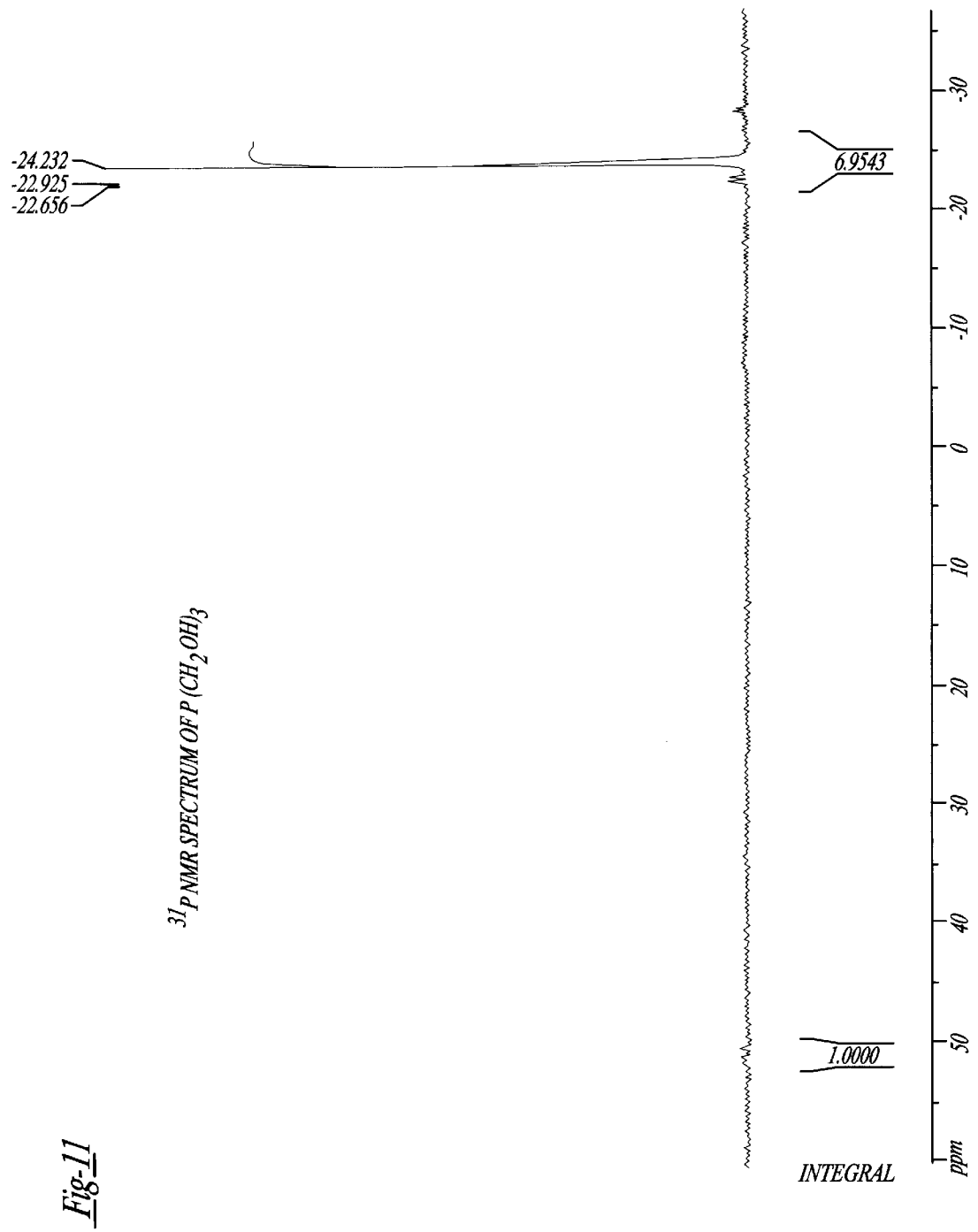
FIG. 11 illustrates the $^{31}$P NMR spectrum of P(CH$_2$OH)$_3$ (compound (1))

The ligand of formula (1) was synthesized by the route depicted in Scheme 1 of FIG. 1. Anhydrous $P(CH_2OH)_4Cl$ (95.25 g, 0.400 moles) was placed in dry triethylamine (600 mL) under $N_2$ atmosphere. The resulting mixture was then heated to 70° C. for one hour and allowed to cool to room temperature. Triethylamine hydrochloride was filtered out and the filtrate collected. The triethylamine solvent was distilled off in vacuo to give the crude product (a mixture of ligand (1) and its hemiacetal adducts) which was then heated at 90° C. for three to four hours under reduced pressure using $N_2$ bleed. The product, a viscous oil or low-melting solid, was obtained in quantitative yield and was found to be >95% pure by $^{31}P$ NMR spectroscopy. Recrystallization was achieved by recrystallizing the product in MeOH at −20° C. The purity of the compound was confirmed by microanalysis, $^1H$ and $^{31}P$ NMR spectroscopy. $^1H$ NMR: doublet at 4.2 ppm, $^{31}P$ NMR −24 ppm as shown in FIG. 11.

The ligand (1) was found to be stable to $O_2$ oxidation in aqueous solutions by $^{31}P$-NMR spectroscopy. A single peak at −24 ppm in the $^{31}P$-NMR spectrum was observed with 1 mg of ligand (1) dissolved in $D_2O$ (aerated). After one hour and twenty-four hour incubations in aerated aqueous solutions, no decrease in the intensity of this peak was observed and no $^{31}P$ signal was observed in the 48 ppm region of the spectrum (i.e., the region where $^{31}P$ in phosphine oxide would resonate) demonstrating the stability of the ligand (1) to $O_2$ oxidation in aqueous solution.

Example 2

A $^{99m}Tc$ chelate with ligand (1) was prepared by mixing 0.1 ml of 0.9% aqueous NaCl (N. saline) containing $^{99m}TcO_4^-$ (0.5–5 mCi) with 0.4 ml of N. saline containing 1 mg/ml of $P(CH_2OH)_3$ and incubating at room temperature (RT) for thirty minutes. The $^{99m}Tc$ product was found to be hydrophilic and cationic by electrophoretic analysis. HPLC analyses were performed using a reversed-phase, PRP-1 column eluted using a gradient. Solvent A=100% 0.01M sodium phosphate at pH 7; solvent B=100% MeCN. The gradient profile was 100% A for two minutes post injection (P.I.) followed by a linear gradient from zero B to 100% B from two minutes to seven minutes P.I., followed by 100% B for an additional six minutes (i.e., until fifteen minutes P.I.). Two peaks were observed; one with a retention time of 1.3 minutes (same as $^{99m}TcO_4^-$) and the other at 4.8 minutes.

The HPLC and electrophoretic analyses indicated that the $^{99m}$Tc chelate is a single species and is formed in >95% yields. This $^{99m}$Tc chelate was found to be stable in aqueous solutions at pH ranging from 4–11 and pH ranging from 7.4–7.8 at 37° C. for ≧24 hr as shown in Table 1.

Referring to Table 1, stability of the $^{99m}$Tc chelate in human serum is also shown. Serum studies were performed by adding 50 μl of the complex solution to 0.95 ml of human serum. Radiochemical purity (RCP) of the complex is shown in Table 1 for time=0, 4, 12, and 24 hours as the mean +/− S.D. (N=5).

Example 3
Bidentate-bishydroxyalkylphosphine Ligands

Two bis-hydroxymethylphosphine ligands were synthesized by the following method (Scheme 3 as shown in FIG. 3). Other bis-hydroxyalkyl phosphine ligands can be synthesized by similar methods.

Figure 12:
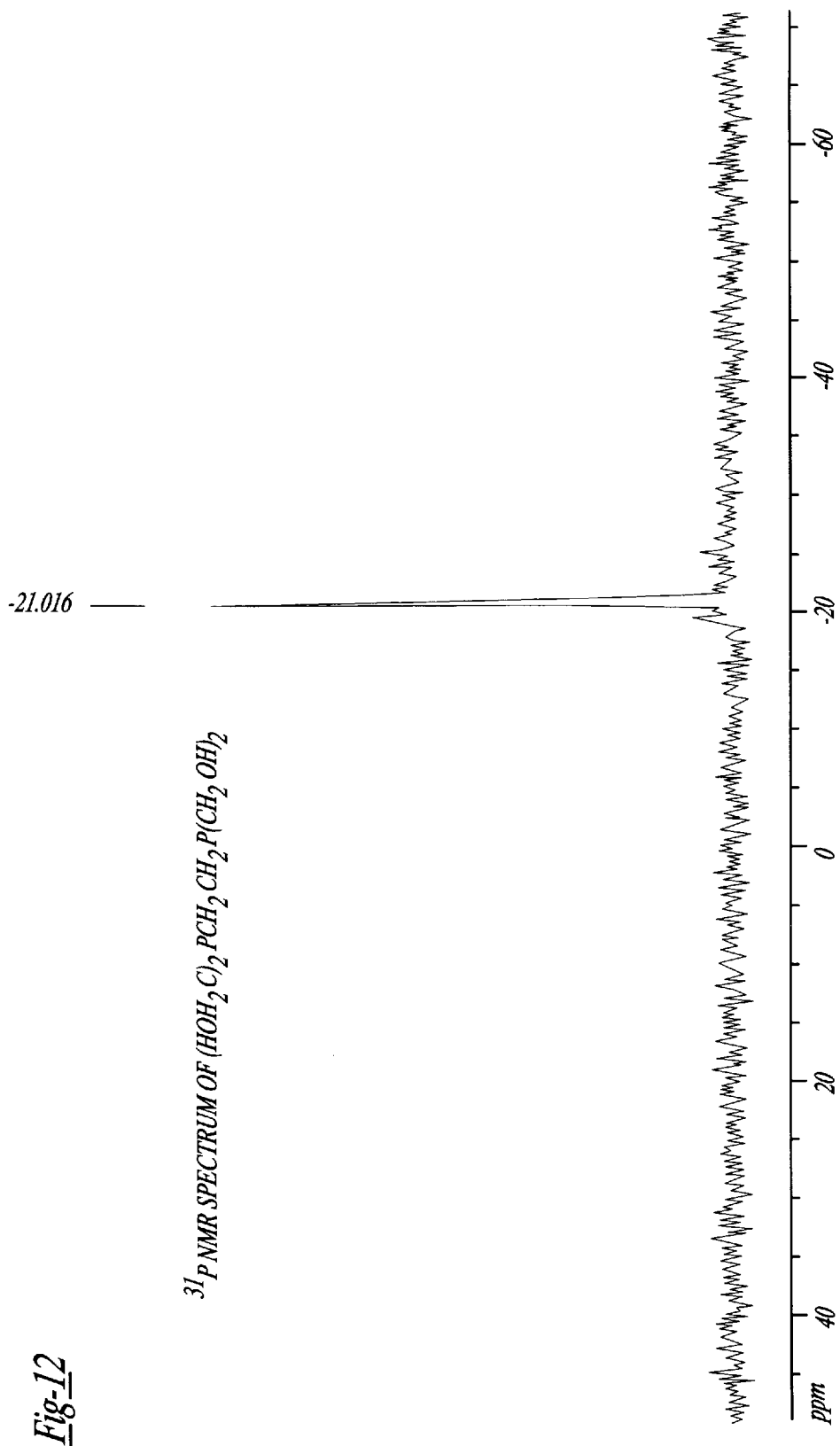
FIG. 12 illustrates the $^{31}$P NMR spectrum of (HOH$_2$C)$_2$PCH$_2$CH$_2$P(CH$_2$OH)$_2$ (compound (3))

Synthesis of 1,2-Bis [bis(hydroxymethyl)phosphino]ethane $(HOH_2C)_2PCH_2CH_2P(CH_2OH)_2$ (3). ("HMPE"). Aqueous formaldehyde (0.233 mol) was placed in 25 mL of deionized oxygen free water and was purged with nitrogen gas for twenty minutes at 25° C. $K_2PtCl_4$ (100 mg) was added to the solution and purging was continued for further ten minutes. 1,2-Bis(phosphino)ethane (5.0 grams, 0.053 mol) was added dropwise to the resultant solution, and stirring was continued for further twenty minutes. Removal of the solvent in vacuo after filtration, yielded the compound 1,2-Bis[bis(hydroxymethyl)phosphino]ethane in near quantitative yield, as a colorless viscous oil. The compound solidified upon standing at room temperature for few days. Anal. Calcd for $C_6H_{16}O_4P_2$: C, 33.65; H, 7.53. Found: C, 33.72; H, 7.45. $^1$H NMR: d 1.52 (m, br, 4H, $CH_2CH_2$), 3.90 (m, br, 8H, $P(CH_2OH)$). $^{31}$P NMR: d −25.1 (s). NMR spectrum is shown in FIG. 12.

Figure 13:
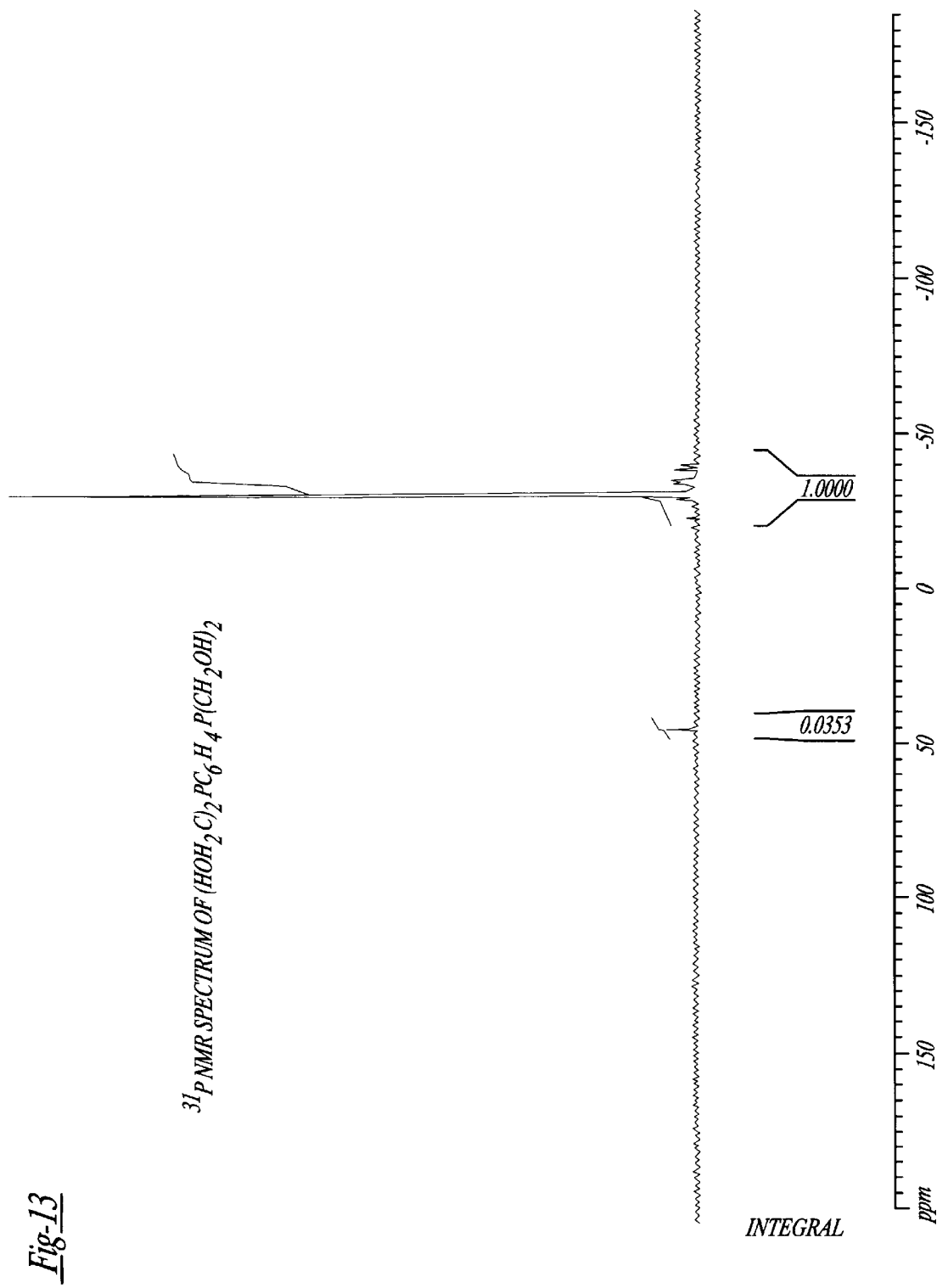
FIG. 13 illustrates the $^{31}$P NMR spectrum of (HOH$_2$C)$_2$PCH$_2$CH$_2$P(CH$_2$OH)$_2$ (compound (4))

Example 4
Synthesis of 1,2-Bis[bis(hydroxymethyl)phosphino]benzene $(HOH_2C)_2PC_6H_4P(CH_2OH)_2$ (4). ("HMPB"). Aqueous formaldehyde (0.160 mol) was placed in 25 mL of deionized oxygen free water and was purged with nitrogen gas for twenty minutes at 25° C. $K_2PtCl_4$ (100 mg) was added to the solution and purging was continued for a further ten minutes. 1,2-Bis(phosphino)benzene (5.0 g, 0.035 mol) was added dropwise to the resultant solution, and stirring was continued for a further twenty minutes. Removal of the solvent in vacuo after filtration, afforded the compound 1,2-Bis[bis(hydroxymethyl)phosphino]benzene in near quantitative yield, as a colorless viscous oil. The compound solidified upon standing at room temperature for few days. Anal. Calcd for $C_{10}H_{16}O_4P_2$: C, 45.81; H, 6.15. Found: C, 45.67; H, 6.25. $^1$H NMR: d 1.61 (m, br, 4H, $CH_2CH_2$), 4.20 (m, br, 8H, $P(CH_2OH)$ ). $^{31}$P NMR: d −31.2 (s). NMR spectrum shown in FIG. 13.

Both compound (3) and compound (4) were found to be stable to $O_2$ oxidation in aqueous solutions by $^{31}$P-NMR spectroscopy. A single peak at −25.1 ppm or −31.2 ppm in the $^{31}$P-NMR spectrum was observed for compounds (3) and (4), respectively. After one hour and twenty-four hour incubation of $10^{-3}$M of compounds (2) or (3) in aerated aqueous solutions, no decrease in the intensity of this peak was detected and no $^{31}$P signal was observed in the 40–50 ppm region of the spectrum, where, naturally oxidized phosphineoxides are observed.

Example 5

Figure 10:
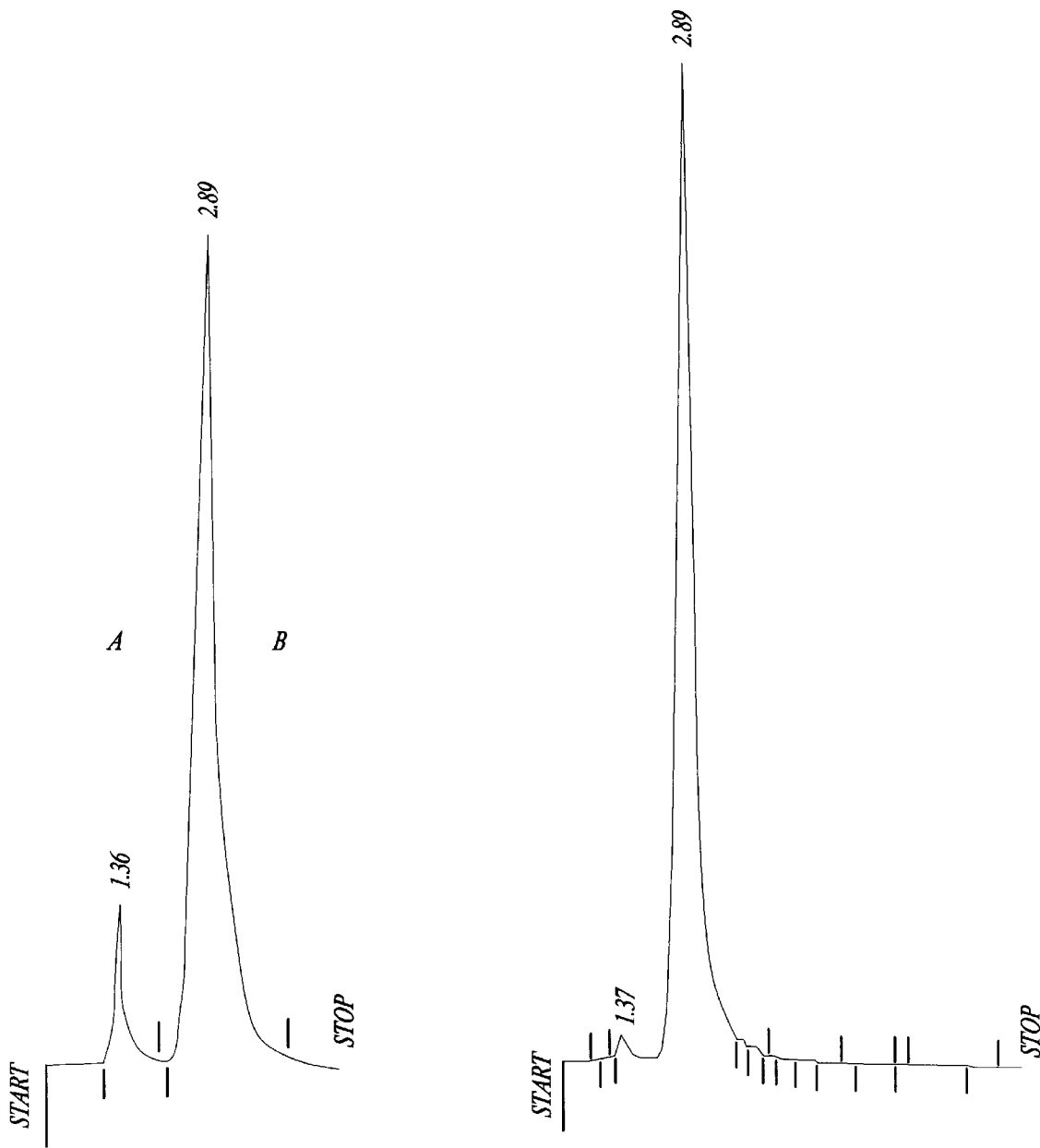
FIG. 10 is a graph showing HPLC analysis of $^{99m}$Tc-dihydroxymethylene-ethylene-phosphine ($^{99m}$Tc-3) having retention times for $^{99m}$TcO$_4$ and $^{99m}$Tc-3 of 1.36 minutes and 2.88 minutes respectively and wherein A: twenty minutes after mixing and B: is four hours after mixing $^{99m}$TcO$_4^{31}$ and 1 mg/mL of (3) at pH 7.

$^{99m}$Tc-chelates of compounds (3) and (4) were prepared by simply mixing 0.1 ml of N. saline containing $^{99m}$TcO$_4^-$ (0.5–5 mCi) with 0.4 ml of N. saline containing 1 mg/ml of compounds (3) or (4) and were incubated at room temperature for one hour. The products were analyzed by electrophoresis and HPLC. HPLC analyses were performed by reversed phase (PRP-1 column) chromatography using the gradient elution system previously described and shown in FIG. 10.

The $^{99m}$Tc-chelates formed with both compounds (3) and (4) were found to be a single cationic species. The retention times of these $^{99m}$Tc-3 is 8.49 minutes and $^{99m}$Tc-4 is 8.43 minutes. HPLC analyses demonstrates that the yield of these products was ≧95% (Table 3). $^{99m}$Tc-chelates with both compounds (3) and (4) were found to be stable in human serum at pH 7.4–7.8 at 37° C. for ≧24 hr (Table 3).

The identical products (as assessed by HPLC and electrophoresis) are produced when $^{99m}$TcO$_4^-$ is reduced with Sn(II) in the presence of 1 mg/ml and either compounds (3) or (4). Using Sn(II) as the reducing agent, the $^{99m}$Tc chelates are formed in >95% yields in <5 minutes.

Example 6
Formation of Complexes with Rhenium

A Re complex with $P(CH_2OH)$ was made by the method depicted in Scheme 2 as shown in FIG. 2.

Synthesis of $[Re(O)_2\{P(CH_2OH)_3\}_4]^+$ (2)

Figure 14:
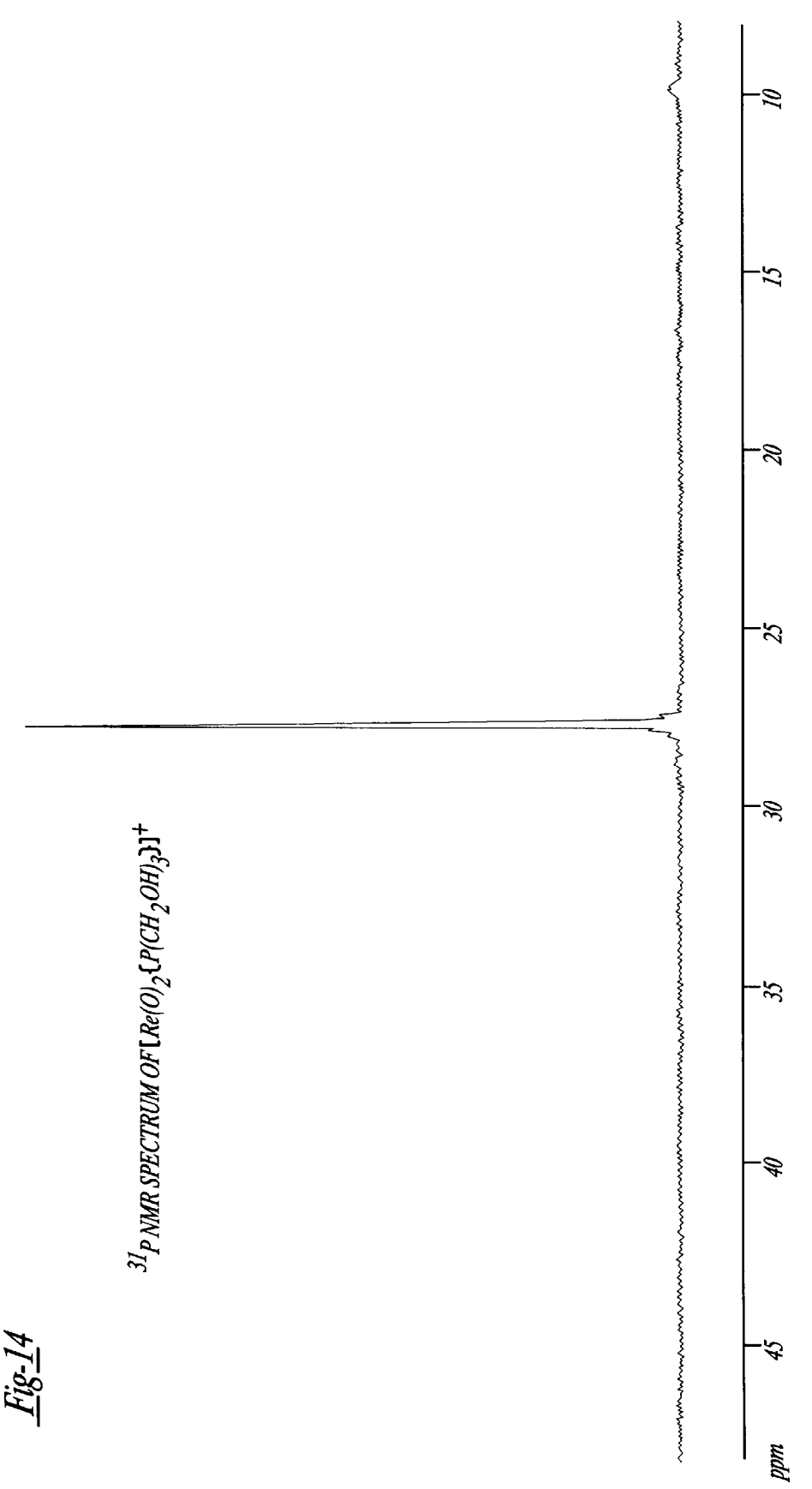
FIG. 14 illustrates the $^{31}$P NMR spectrum of [Re(O)$_2$[P(CH$_2$OH$_3$)]$^+$ (compound (2))

An aqueous solution (20 mL) of 2.0 mmol $P(CH_2OH)_3$ was added dropwise to a rhenium precursor $Re(O)_2I(PPh_3)_2$ (1.0 mmol) in dichloromethane (20 mL) at 25° C. with constant stirring. The stirring was continued for two hours and the aqueous layer was separated from an organic layer. The aqueous solution was concentrated to ~5 mL in vacuo and evaporated slowly at room temperature to afford yellow colored complex (2) 90% yield. Anal. Calcd for $C_{12}H_{36}O_{14}P_4ReI$: C, 17.13; H, 4.31. Found: C, 17.43; H, 4.46. $^1$H NMR: d 4.30 (m, $P(CH_2OH)$). $^{31}$P NMR: 27.7(s). NMR spectrum shown in FIG. 14.

Examples of Formation of Rhenium Complexes

Rhenium complexes of formed with compounds (3) and (4) were synthesized and characterized.

Example 7
Synthesis of $[Re(O)_2\{(HOH_2C)_2PCH_2CH_2P(CH_2OH)_2\}_2]^+$ (5)

Figure 15:
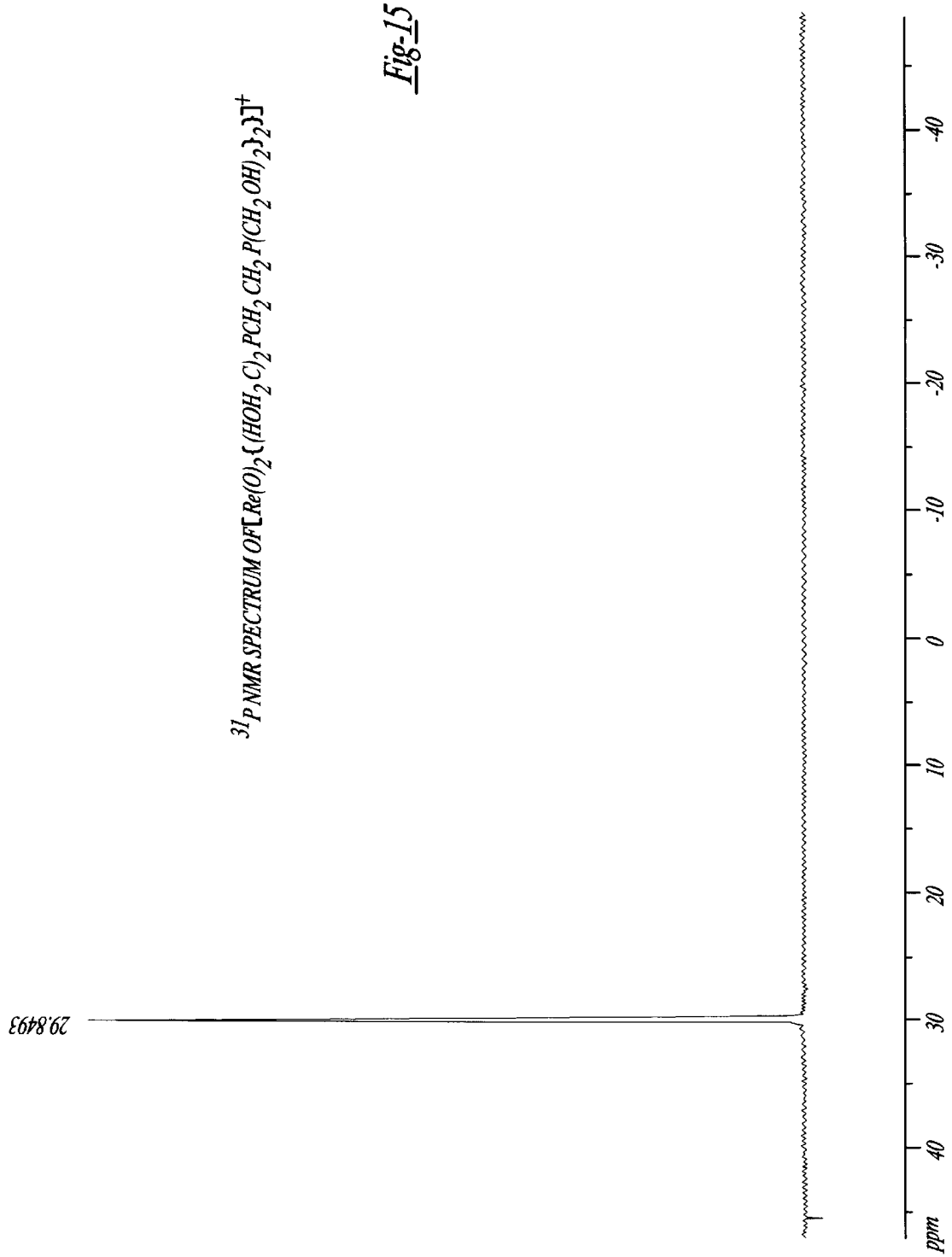
FIG. 15 illustrates the $^{31}$P NMR spectrum of [Re(O)$_2$\{(HOH$_2$C)$_2$PCH$_2$CH$_2$P(CH$_2$OH)$_2$\}$_2$]+ (compound (5))

An aqueous solution (20 mL of 2.0 mmol) of the ligand HMPE (3) was added dropwise to a rhenium precursor $[Re(O)_2(C_5H_6N)_4]Cl$ (1.0 mmol) also in water (20 mL) at 25° C. with constant stirring. The stirring was continued for thirty minutes and the solution was then concentrated to ~5 mL in vacuo and evaporated slowly at room temperature to give crystalline complex (5) in 85% yield as described in Scheme 4 of FIG. 4. The crystal structure of complex (5) is shown in FIG. 8. Anal. Calcd for $C_{12}H_{32}O_{10}P_4ReI$: C, 18.64; H, 4.17. Found: C, 18.68; H, 4.21. $^1$H NMR: δ2.28 (m, 8H, $CH_2CH_2$), 4.40 (m, 16H, $P(CH_2OH)$). $^{31}$P NMR: δ29.8(s). NMR spectrum shown in FIG. 15.

The above complex can also be synthesized by the reaction of $[Re(O)_2I(PPh_3)_2]$ in dichloromethane and the ligand (3) (1:2 mmol), as shown in Scheme 3 of FIG. 3, in aqueous media by stirring at room temperature for thirty minutes.

Example 8
Synthesis of $[Re(O)_2\{(HOH_2C)_2PC_6H_4P(CH_2OH)_2\}_2]^+$ (6)

Figure 9:
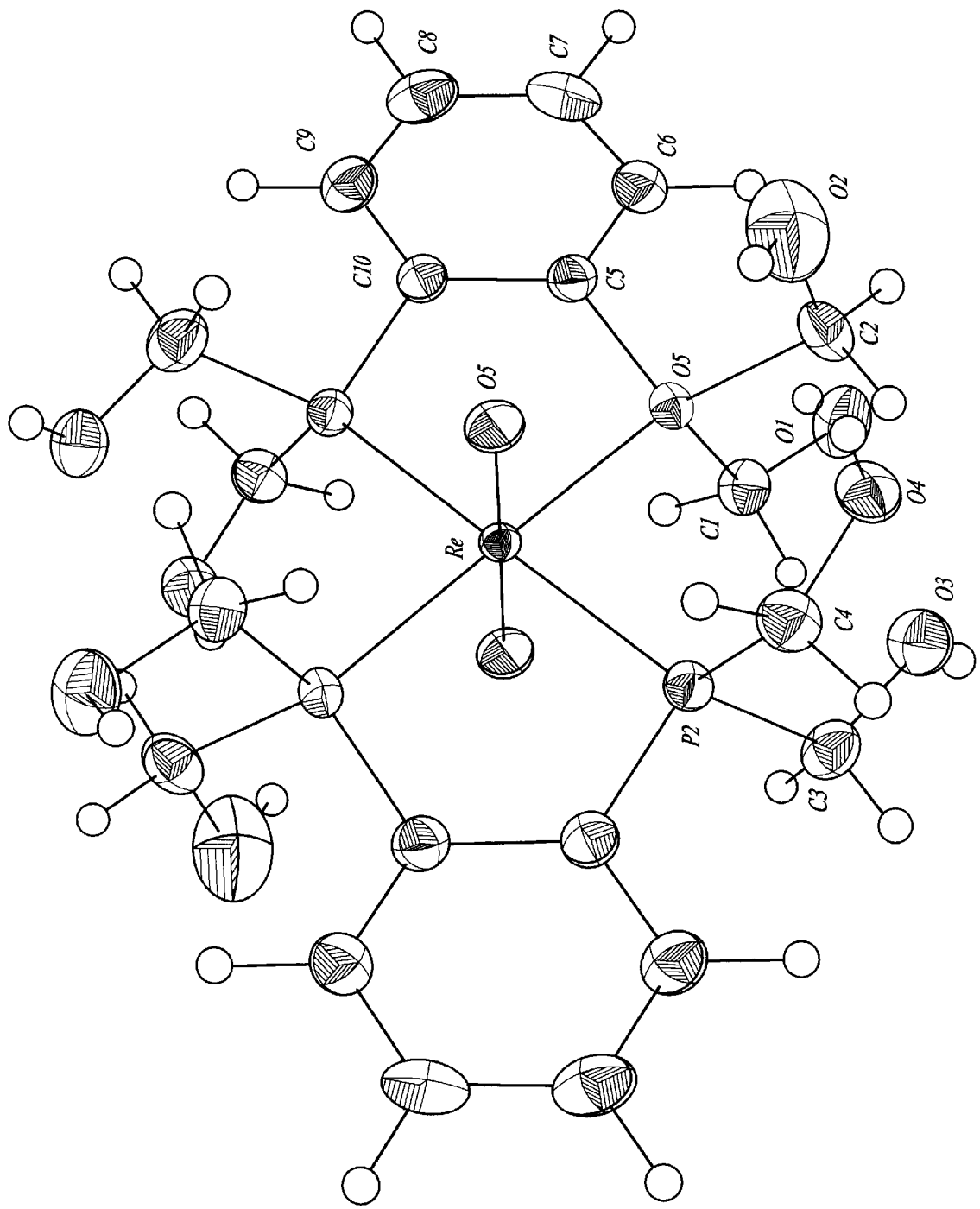
FIG. 9 illustrates the crystal structure of compound (6)
Figure 16:
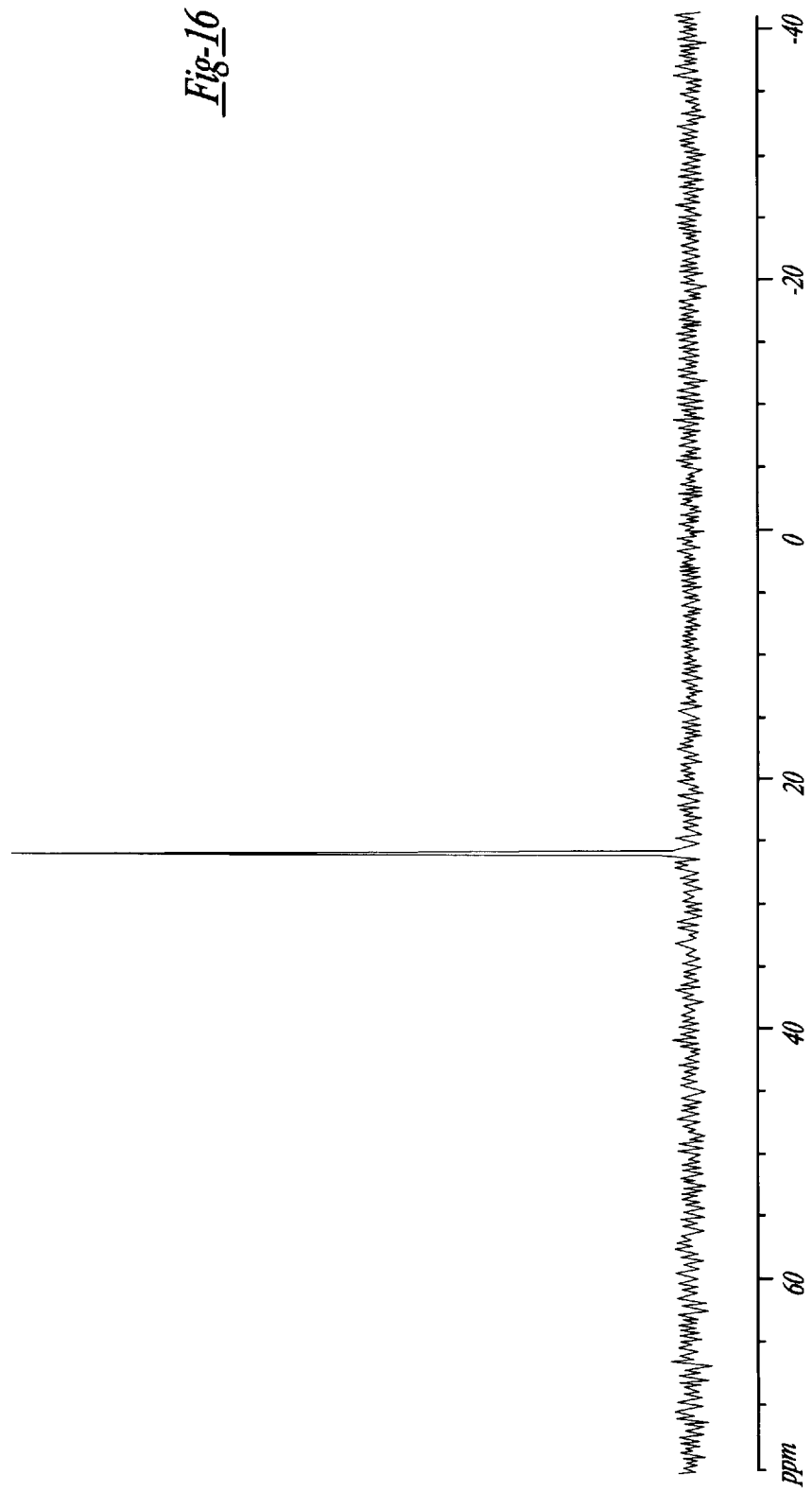
FIG. 16 illustrates the $^{31}$P NMR spectrum of [Re(O)$_2$\{(HOH$_2$C)$_2$PC$_6$H$_4$P(CH$_2$OH)$_2$\}$_2$]+ (compound (6)).

An aqueous solution (20 mL of 2.0 mmol) of the ligand HMPB (4) was added dropwise to a rhenium precursor $Re(O)_2I(PPh_3)_2$ (1.0 mmol) in dichloromethane (20 mL) at 25° C. with constant stirring. The stirring was continued for thirty minutes and the aqueous layer was separated from the organic layer. The aqueous solution was concentrated to ~5 mL in vacuo and evaporated slowly at room temperature to give crystalline complex (6) 85% yield (Scheme 5 as shown in FIG. 5). The crystal structure of complex (5) is shown in FIG. 9. Anal. Calcd for $C_{20}H_{32}O_{10}P_4ReI$: C, 27.63; H, 3.71. Found: C, 27.73; H, 3.76. NMR: δ 4.20 (m, 16H, P(CH$_2$OH)) 7.8 (m, 8H, $C_6H_4$). $^{31}$P NMR: δ24.2(s). NMR spectrum is shown in FIG. 16.

The above complex can also be synthesized by the reaction of [Re(O)$_2$(C$_5$H$_6$N)$_4$]Cl and the ligand 4 (1:2 mmol) in aqueous solution by refluxing for two hours.

These data demonstrate that the Re complex with the ligands (3) and (4) have Re(V) present as the trans-dioxo core and each Re-chelate has two (3) or (4) ligands attached according to Schemes 4 and 5 (see FIGS. 4 and 5). When the ReO$_2$(3)$_2$ and ReO$_2$(3)$_2$ were analyzed by reversed phase HPLC, the compounds exhibited retention times of 8.45 minutes and 8.50 minutes, respectively. Since these retention times are identical to the $^{99m}$Tc complexes with ligands (3) and (4), respectively, the $^{99m}$Tc complexes can be assigned the same structure as both Re-complexes.

The final confirmation of the structures of the Rhenium complexes of ligands (3) and (4) were determined through X-ray crystallographic analysis.

Example 9

Formation of a Ligand Containing Six Phosphine Groups

Referring to Scheme 7 of FIG. 6, synthesis of a ligand containing six phosphine groups that will chelate $^{99m}$Tc in high yields in accordance with the present invention is shown. Compounds (11) and (12) were synthesized by the route depicted in Scheme 7, generally shown in FIG. 7, and were characterized by $^1$H and $^{31}$P NMR spectroscopy.

Compound (12) shown in FIG. 6 was prepared by the reduction of compound (11) with formaldehyde in methanol. The ligand compound (12) was characterized by $^{31}$P and $^1$H NMR spectroscopy. 100 μl of N. saline containing 0.5–2 mCi $^{99m}$TcO$_4^-$ was added to 400 μl of a N. saline solution containing 1 mg/ml of compound (5) as shown in FIG. 4. After incubating at room temperature for five minutes the complex yield was found to be >95% using two strip paper chromatographic method using acetone to develop one strip and 0.9% aqueous NaCl as the eluent for the second strip. HPLC analysis showed a retention time of 4.3 minutes. These results demonstrate that compound (12) is able to rapidly reduce $^{99m}$TcO$_4^-$ (without the presence of an external reducing agent) and rapidly form a $^{99m}$Tc chelate in high yields. This $^{99m}$Tc chelate was shown to be stable in N. saline and in human serum for ≧24 hours as shown in Tables 1–3.

Example 10

Ligands Containing Hydroxyalkylphosphine Group(s) and Other Chelating Atoms Several examples of ligands containing ≧3 atoms or groups that form stable complexes with $^{99m}$Tc or $^{186/188}$Re can be synthesized. For example, ligands containing two hydroxyalkylphosphine donor groups and two other donor atoms can be characterized by the following formula:

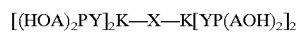

where A=—CH$_2$—, —(CH$_2$)$_2$—, iso- or normal-C$_3$H$_6$, K includes donor atoms or groups which are used to complex with $^{99m}$Tc, $^{186/188}$Re, and $^{105}$Rh and are selected from the group consisting of —N(R)—, —NH, —S—, and Ag. Y=—CH$_2$—, —(CH$_2$)$_2$—, iso- or normal-C$_3$H$_6$—X includes —CH$_2$—, —(CH$_2$)$_2$—, —(CH$_2$)$_3$—, —(CH$_2$)$_4$—, —CH$_2$CHR—, —CH$_2$CHRCH$_2$—, —CHRCH$_2$CH$_2$—, a substituted aromatic group containing a side arm R'. R and R' can be the same or different and can be H and/or side chains containing a functional group such as —OH, NH$_2$, COOH, —SH and other groups which can be used for conjugation of the uncomplexed or "preformed" $^{99m}$Tc- or $^{186/188}$Re chelate to biomolecular targeting structures. Methods and groups that can be used for conjugation involve activation of functional groups (e.g., to activated esters, N-hydroxy-succinimides, benzylisothiocyanate, alkylhalides, (CDI, etc.) using approaches previously described (Marmion et al., 1994; Meares et al., 1988; Parker, 1990).

Example 11

A second example of a multi-dentate ligand containing two hydroxyalkyl phosphine groups and other donor atoms or groups can be characterized by the following formula:

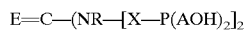

where X=—CH$_2$—, (CH$_2$)$_2$, —C$_3$H$_6$—, and A=—CH$_2$—, (CH$_2$)$_2$, —C$_3$H$_6$— and E=O or S. R can be the same or different and can include H.

Examples of the utility of the compounds of the present invention have also been shown.

The biodistribution of $^{99m}$Tc-P(CH$_2$OH)$_3$ in anesthetized rats (Sprague-Dawley rats anesthetized intraperitoneally with 50 mg/kg of Na-pentobarbital) (Table 2) at two minutes and thirty minutes post-injection (intravenous injection) showed the route of clearance is primarily into the urine via the kidneys with some clearance by the liver with excretion into the intestines. No evidence of in vivo dissociation of the chelate to form $^{99m}$TcO$_4^-$ is evident since the amount of $^{99m}$Tc activity found in the stomach was minimal (Table 2). These data provide evidence that mono-dentate hydroxyalkyl phosphines can form $^{99m}$Tc-chelate(s) that have excellent in vitro (pH 4–11) and in vivo stability. Furthermore, the fact that a $^{99m}$Tc chelate was formed by simply mixing $^{99m}$TcO$_4^-$ with P(CH$_2$)OH)$_3$ in saline is evidence that this phosphine ligand is capable of reducing $^{99m}$Tc from the +7 oxidation state in pertechnetate to a lower oxidation state that is able to chelate with other P(CH$_2$OH)$_3$ molecules present in excess.

The biodistribution of the $^{99m}$Tc chelates with compounds (3) and (4) in anesthetized rats (Tables 4 and 5) demonstrate that these chelates clear primarily into the urine via the kidney with some uptake and clearance via the liver. No evidence of in vivo dissociation of the chelate to form $^{99m}$TcO$_4^{31}$ is evident since the amount of activity found in the stomach is minimal (Tables 4 and 5). These data provide evidence that the $^{99m}$Tc chelates with both compounds (3) and (4) have excellent in vitro and in vivo stability. Furthermore, the fact that these chelates were formed by simply mixing $^{99m}$TcO$_4^-$ with either compound (2) or compound (3) in aerated saline evidences that these hydroxyalkylphosphine groups are capable of reducing $^{99m}$Tc from the +7 oxidation state in pertechnetate to a lower Tc-oxidation state that is able to chelate other compound (3) and (4) ligands present as excess in the solutions.

Throughout this application various publications are referenced by citation or number. Full citations for the publications referenced by number are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Complex yields and in vitro Stability of the $^{99m}$Tc complex resulting from the reaction of $P(CH_2OH)_3$, 1. with $^{99m}TcO_4^-$.

| Time (hrs) | Complexation yields in %* | | | |
|---|---|---|---|---|
| pH* | 0 | 4 | 12 | 24 |
| 4 | 98 ± 1 | 98 ± 1 | 97 ± 1.2 | 96 ± 2 |
| 7 | 98 ± 1 | 98 ± 1 | 97 ± 1.3 | 96 ± 2.2 |
| 9 | 98 ± 1 | 98 ± 1 | 96 ± 1 | 96 ± 2 |
| 11 | 98 ± 1.2 | 98 ± 1 | 96 ± 1.3 | 96 ± 2 |
| 13 | 95 ± 1.4 | 95 ± 1.5 | 92 ± 1.5 | 90 ± 1.7 |
| Stability in Human Serum at 37° C. | | | | |
| 7.4–7.8 | 98 ± 1.5 | 98 ± 1.7 | — | 97 ± 1.5 |

*The complex ($^{99m}$Tc-1) formed at neutral pH (pH 6–7.5) by mixing 1 ml of 1 mg/ml of $P(CH_2OH)_3$, in N. saline and 0.1 ml of $^{99m}TcO_4^-$-(0.1–2 mCi) in N. saline at room temperature. The pH of each solution was adjusted after formation of the complex. Serum stability studies were performed by adding 50 μl of the complex solution to 0.95 ml of human serum. The radiochemical purity (RCP) at 0, 4, 12 and 24 hr is reported as the mean ± SD (N = 5).

TABLE 2

Stability of $^{99m}$Tc-3 in Human Serum at 37° C. as a Function of Time

| Time (Hr) | RCP* | Time (hr) | RCP* |
|---|---|---|---|
| 1 | 98.9 ± 0.4 | 23 | 94.2 ± 0.5 |
| 4 | 97.2 ± 1.0 | 50 | 91.5 ± 1.5 |
| 7 | 96.2 ± 0.4 | 74 | 95.8 ± 2.0 |

*RCP = Radiochemical Purity or the percent of the $^{99m}$Tc-3 complex remaining intact in the serum at different incubation times.

TABLE 3

Complex yields and in vitro stability of the $^{99m}$Tc complex resulting from the reactions of 3 and 4 respectively with $TcO_4^-$

| Time | % Complexation Yield* | |
|---|---|---|
| (hrs) | $^{99m}$Tc-3 | $^{99m}$Tc-4 |
| 0 | 97 ± 1.3 | 98 ± 1.7 |
| 4 | 98 ± 1.1 | 98 ± 1.2 |
| 12 | 97 ± 1.0 | 97 ± 1.4 |
| 24 | 97 ± 1.4 | 98 ± 1.2 |
| Stability in Human Serum at 37° C. | | |
| 24 | 98 ± 1.8 | 96 ± 1.2 |

*The $^{99m}$Tc-complexes with 2 and 3 (i.e., $C_2H_4[P(CH_2OH)_2]_2$ and O-phenyl $[P(CHOH)_2]_2$, respectively) formed at neutral pH (pH 6–7.5) by mixing 1 ml of 1 mg/ml of of 2 or 3 in N. saline and 0.1 ml of $^{99m}TcO_4^-$-(0.1–2 mCi) in N. saline at room temperature. The pH of each solution was adjusted after formation of the complex. Serum stability studies were performed by adding 50 μl of the complex solution to 0.95 ml of human serum. The RCP at 0, 4, 12 and 24 hr is reported as the mean ± SD (N = 5).

TABLE 4

Biodistribution of $^{99m}$Tc-dihydroxymethylene-ethylene-phosphine ($^{99m}$Tc-3) in anesthetized rats[a] as a function of time ater IV injection.

| | Percent Injected Dose (ID) per Organ[b] | | |
|---|---|---|---|
| Organ | 30 min | 1 hr | 2 hr |
| Brain | 0.04 ± 0.01 | 0.03 ± 0.01 | 0.01 ± 0.01 |
| Blood | 4.45 ± 0.70 | 2.54 ± 0.40 | 0.96 ± 0.18 |
| Heart | 0.09 ± 0.01 | 0.05 ± 0.01 | 0.01 ± 0.01 |
| Lung | 0.38 ± 0.11 | 0.23 ± 0.09 | 0.10 ± 0.03 |
| Liver | 2.92 ± 0.36 | 2.68 ± 0.28 | 1.87 ± 0.13 |
| Spleen | 0.04 ± 0.01 | 0.03 ± 0.01 | 0.02 ± 0.01 |
| Stomach | 0.31 ± 0.07 | 0.24 ± 0.06 | 0.12 ± 0.05 |
| Large Intestine | 0.52 ± 0.06 | 0.36 ± 0.05 | 0.13 ± 0.07 |
| Small Intestine | 1.65 ± 0.08 | 1.77 ± 0.20 | 1.39 ± 0.64 |
| Kidneys | 2.67 ± 0.40 | 2.02 ± 0.34 | 1.36 ± 0.52 |
| Bladder | 61.1 ± 4.0 | 72.3 ± 2.9 | 87.9 ± 4.3 |

[a]Sprague-Dawley rats (180–240 g) anesthetized with Na-pentobarbital (50 mg/kg-IP) were injected intravenously.
[b]% ID/organ values are mean ± SD; n = 5 for each group; % ID in whole blood estimated assuming whole blood volume is 6.5% of body weight.

TABLE 5

Biodistribution of $^{99m}$Tc-dihydroxymethyl-phenyl-phosphine ($^{99m}$Tc-4) in anesthetized rats[a] as a function of time after IV injection.

| | Percent Injected Dose (ID) per Organ[b] | | |
|---|---|---|---|
| Organ | 30 min | 1 hr | 2 hr |
| Brain | 0.02 ± 0.01 | 0.01 ± 0.02 | 0.01 ± 0.01 |
| Blood | 2.94 ± 0.83 | 1.74 ± 0.37 | 1.32 ± 0.97 |
| Heart | 0.09 ± 0.02 | 0.04 ± 0.01 | 0.04 ± 0.03 |
| Lung | 0.26 ± 0.13 | 0.18 ± 0.08 | 0.12 ± 0.09 |
| Liver | 8.15 ± 2.17 | 5.06 ± 1.52 | 3.56 ± 1.53 |
| Spleen | 0.05 ± 0.01 | 0.03 ± 0.01 | 0.02 ± 0.01 |
| Stomach | 0.36 ± 0.18 | 0.38 ± 0.27 | 0.40 ± 0.30 |
| Large Intestine | 0.31 ± 0.14 | 0.22 ± 0.08 | 0.16 ± 0.10 |
| Small Intestine | 43.80 ± 6.22 | 49.41 ± 3.83 | 47.68 ± 8.11 |
| Kidneys | 4.44 ± 3.62 | 3.39 ± 1.52 | 2.99 ± 2.22 |
| Bladder | 29.8 ± 6.9 | 33.6 ± 6.9 | 40.5 ± 8.2 |

[a]Sprague-Dawley rats (180–240 g) anesthetized with Na-pentobarbital (50 mg/kg-IP) were injected intravenously.
[b]% ID/organ values are mean ± SD; n = 5 for each group; % ID in whole blood estimated assuming whole blood volume is 6.5% of body weight.

REFERENCES

Abrams et al., "Technetium-99m-human polyclonal IgG radiolabeled via the Hydrazino Nicotinamide derivative for imaging focal sites of infection in rats" *J Nucl Med* 31:2022–2028, 1990a.

Abrams et al., "Synthesis and crystal and molecular structure of a Technetium-Hydralazino complex [TcCl$_2$ (C$_8$H$_5$N$_4$)$_2$] G0.75C$_7$H$_8$" *Inorg Chim Acta* 173:133–135, 1990b.

Chianelli et al., "$^{99m}$Tc-interleukia-2: a new radiopharmaceutical for the in vivo detection of lymphocytic infiltration" *J Nucl Biol Med* 38:476, 1994.

Deutsch, "Aspects of the chemistry of technetium phosphine complexes" *Radiochim Acta* 63:195–197, 1993.

Ellis et al., "Water-soluble Tris(hydroxymethyl) phosphine complexes with Nickel, Palladim and Platinum. Crystal structure of [Pd{P(CH$_2$OH)$_3$}$_4$•CH$_3$OH" *Inorg Chem* 31:3026–3033, 1992.

Fritzberg et al., "Specific and stable labeling of antibodies with $^{99m}$Tc with a dimide dithiolate chelating agent" *Proc. Natl. Acad. Sci., USA* 85:4025–4029, 1988.

Gustavson et al., "Synthesis of a new class of Tc-chelating agents" N$_2$S$_2$ monoaminemonoamide (MAMA) ligands" *Tetrahedron Lett*, 32:5485–5488, 1991.

Jurisson et al, "Coordination compounds in nuclear medicine" *Chem Rev* 93:1137–1156, 1993.

Kelly et al., *J Nucl Med* 34:222–227, 1993.

Knight et al. "Thrombus imaging with $^{99m}$Tc synthetic peptides based upon the binding domain of a monoclonal antibody to activated platelets" *J Nucl Med* 35:282–288, 1994.

Lister-James et al., "A structure-activity-relationship (SAR) study of somatostatin receptor-binding peptides radiolabeled with $^{99m}$Tc" *J Nucl Med*, 35:257–258P, 1994.

Marmion et al., "Radiopharmaceutical development of TechneScan Q-12" *J Nucl Biol Med* 38:455–456, 1994.

Meares et al., "Chelate radiochemistry: cleavable linkers lead to altered levels of radioactivity in the liver" *Int J Cancer* 2:99–102, 1988.

Muna et al., "Synthesis, radiochemical and biological evaluation of $^{99m}$Tc[N4(O)Phe]-octreotide, a new octreotide derivative with high affinity for somatostatin receptors" *J Nucl Bio Med* 38:452, 1994.

Noch et al., "$^{99m}$Tc-N$_4$-Lys-Biotin, a new biotin derivative useful for pretargeted avidin-biotin immunoscintigraphy, synthesis, radiochemistry and biological evaluation" *J Nucl Biol Med* 38:460, 1994.

Nowotnik and Nunn, "Technetium SPECT agents for imaging heart and brain" *DN and P* 5:174–183, 1992.

Parker, "Tumor targeting with radiolabeled macrocycle-antibody conjugates" *Chem. Soc. Rev.* 19:271–291, 1990.

Pasqualine et al., "Bis(dithiocarbamot)nitrido $^{99m}$Tc radiopharmaceuticals: a class of neutral myocardial imaging agents" *J Nucl Med* 35:334–331, 1994.

Rao et al., "Kinetics and mechanism of reactions of S-protected dithiol monoaminemonoamide (MAMA) ligands with technetium" *Nucl Med Biol*, 19:889–895, 1992.

Troutner, *Nucl Med Biol* 14:171.

Volkert et al., "Therapeutic radio-nuclides: production and decay property considerations" *J Nucl Med* 32:174–185, 1991.

Wilbur, "Radiohalogenation of proteins: an overview of radionuclides, labeling methods and reagents for conjugate labeling" *Bioconj Chem* 3:433–470, 1992.

What is claimed is:

1. A compound for use as a diagnostic or therapeutic pharmaceutical, said compound consisting essentially of:
   a ligand consisting essentially of at least one hydroxyalkyl phosphine donor group bound to a metallic radionuclide selected from the group consisting of $^{186}$Re, $^{188}$Re, and $^{99m}$Tc to form a metal-ligand complex which is stable in aqueous solutions containing oxygen, serum and other body fluids.

2. A compound as set froth in claim 1, wherein said ligand is monodentate of the formula:

$$P(AOH)_3$$

wherein A is —CH$_2$—, —C$_2$H$_4$—, or iso- or normal-C$_3$H$_6$—.

3. A compound as set forth in claim 1, wherein the ratio of ligand to metal is greater than or equal to 1:1.

4. A compound for use as a diagnostic or therapeutic pharmaceutical, said compound consisting essentially of:
   a ligand consisting essentially of at least one hydroxyalkyl phosphine donor group bound to a metallic radionuclide selected from the group consisting of $^{186}$Re, $^{188}$Re, and $^{99m}$Tc to form a metal-ligand complex which is stable in aqueous solutions containing oxygen, serum and other body fluids, said compound being of the formula:

$$M^R\text{-}[P(A\text{-}OH)_3]_x$$

where M is a transition metal; $M^R$ is a transition metal in a reduced oxidation state as compared to M; X is 1–6; and A is an alkyl group.

* * * * *